(12) United States Patent
Liao et al.

(10) Patent No.: US 11,492,374 B2
(45) Date of Patent: *Nov. 8, 2022

(54) PEPTIDES FOR TREATMENT OF MEDICAL DISORDERS

(71) Applicant: Humanwell Pharmaceutical US, Ballwin, MO (US)

(72) Inventors: Subo Liao, Ballwin, MO (US); Jun Yang, Ballwin, MO (US); Jinliang Lv, Yichang (CN); Zongquan Liao, Yichang (CN); Hao Zhou, Yichang (CN); Jueyuan Gao, Yichang (CN); Tianpeng Xie, Yichang (CN); Quanli Yang, Yichang (CN)

(73) Assignee: Humanwell Pharmaceutical US, Ballwin, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/911,701

(22) Filed: Jun. 25, 2020

(65) Prior Publication Data

US 2021/0403505 A1   Dec. 30, 2021

(51) Int. Cl.
| C07K 1/10 | (2006.01) |
| C07K 5/103 | (2006.01) |
| C07K 1/06 | (2006.01) |
| A61K 38/00 | (2006.01) |

(52) U.S. Cl.
CPC .............. *C07K 5/101* (2013.01); *C07K 1/061* (2013.01); *C07K 1/10* (2013.01); *A61K 38/00* (2013.01)

(58) Field of Classification Search
CPC .......... C07K 5/101; C07K 1/10; C07K 1/061; A61K 38/00
See application file for complete search history.

(56) References Cited

U.S. PATENT DOCUMENTS

| 4,406,202 | A | 9/1983 | Salje et al. |
| 5,492,894 | A | 2/1996 | Bascom et al. |
| 5,965,701 | A | 10/1999 | Junien et al. |
| 7,402,564 | B1 | 7/2008 | Schteingart et al. |
| 7,713,937 | B2 | 5/2010 | Schteingart et al. |
| 7,727,963 | B2 | 6/2010 | Schteingart et al. |
| 7,842,662 | B2 | 11/2010 | Schteingart et al. |
| 8,217,007 | B1 | 7/2012 | Schteingart et al. |
| 8,236,766 | B2 | 8/2012 | Schteingart et al. |
| 8,486,894 | B2 | 7/2013 | Schteingart et al. |
| 8,507,649 | B2 | 8/2013 | Lintner et al. |
| 8,536,131 | B2 | 9/2013 | Schteingart et al. |
| 8,906,859 | B2 | 12/2014 | Schteingart et al. |
| 8,951,970 | B2 | 2/2015 | Schteingart et al. |
| 9,321,810 | B2 | 4/2016 | Schteingart et al. |
| 9,334,305 | B2 | 5/2016 | Schteingart et al. |
| 9,359,399 | B2 | 6/2016 | Schteingart et al. |
| 10,004,749 | B2 | 6/2018 | Hsu |
| 10,017,536 | B2 | 7/2018 | Schteingart et al. |
| 10,035,767 | B2 | 7/2018 | Murayama et al. |
| 10,138,270 | B2 | 11/2018 | Schteingart et al. |
| 10,653,700 | B2 | 5/2020 | Hsu |
| 10,766,925 | B2 | 9/2020 | Vardanyan et al. |
| 2004/0162242 | A1 | 8/2004 | Olson et al. |
| 2009/0156508 | A1 | 6/2009 | Schteingart et al. |
| 2010/0075910 | A1 | 3/2010 | Schteingart et al. |
| 2011/0212882 | A1 | 9/2011 | Schteingart et al. |
| 2015/0150935 | A1 | 6/2015 | Chalmers et al. |
| 2016/0250277 | A1 | 9/2016 | Chalmers et al. |
| 2017/0183307 | A1 | 6/2017 | Murayama et al. |
| 2017/0231979 | A1 | 8/2017 | Steiner et al. |
| 2018/0028594 | A1 | 2/2018 | Chalmers et al. |
| 2018/0078605 | A1 | 3/2018 | Spencer et al. |
| 2019/0144499 | A1 | 5/2019 | Li et al. |
| 2020/0054594 | A1 | 2/2020 | Niu et al. |
| 2020/0085961 | A1 | 3/2020 | Wilson et al. |

FOREIGN PATENT DOCUMENTS

| CN | 107098871 A | 8/2017 |
| CN | 109280075 A | 1/2019 |
| CN | 109280076 A | 1/2019 |
| CN | 109879934 A | 6/2019 |
| JP | 5807140 B1 * | 11/2015 |
| WO | 9932510 A1 | 7/1999 |
| WO | 0110890 A2 | 2/2001 |
| WO | 02060432 A1 | 8/2002 |
| WO | 03105677 A2 | 12/2003 |
| WO | 2007120614 A2 | 10/2007 |
| WO | 2007139826 A2 | 12/2007 |
| WO | 2007139921 A2 | 12/2007 |
| WO | 2008057608 A2 | 5/2008 |
| WO | 2010057961 A1 | 5/2010 |
| WO | 2012092367 A1 | 7/2012 |

(Continued)

OTHER PUBLICATIONS

Barber A., et al., "Novel Developments with Selective Non-Peptidic Kappa-Opioid Receptor Agonists," Expert Opinion Investigational Drugs, 1997, vol. 6, No. 10, pp. 1351-1368.

Dehaven-Hudkins D.L., et al., "Peripherally Restricted Opioid Agonists as Novel Analgesic Agents," Current Pharmaceutical Design, 2004, vol. 10, pp. 743-757.

Fishbane S., et al., "A Phase 3 Trial of Difelikefalin in Hemodialysis Patients with Pruritus," The New England Journal of Medicine, 2020, vol. 382, No. 3, pp. 222-232.

Hesselink J.M.K., "CR845 (Difelikefalin), A Kappa Receptors Agonist in Phase III by CARA Therapeutics: A Case of 'Spin' in Scientific Writing?," Journal of Pharmacology & Clinical Research, Mar. 10, 2017, vol. 2, No. 3, pp. 001-010.

Inan S., et al., "Kappa Opioid Agonists Suppress Chloroquine-Induced Scratching in Mice," European Journal of Pharmacology, 2004, vol. 502, pp. 233-237.

(Continued)

*Primary Examiner* — Sudhakar Katakam
(74) *Attorney, Agent, or Firm* — Polsinelli PC

(57) ABSTRACT

The present invention provides compounds which are selective kappa-opioid receptor agonist, method of preparation of these compounds, compositions that comprise these compounds, and methods for treating kappa-opiod receptor agonist related medical disorders.

22 Claims, 1 Drawing Sheet

(56) References Cited

FOREIGN PATENT DOCUMENTS

| | | |
|---|---|---|
| WO | 2012118780 A2 | 9/2012 |
| WO | 2016073443 A2 | 5/2016 |
| WO | 2016181408 A2 | 11/2016 |
| WO | 2017151866 A1 | 9/2017 |
| WO | 2017180535 A1 | 10/2017 |
| WO | 2017180659 A1 | 10/2017 |
| WO | 2017201433 A1 | 11/2017 |
| WO | 2017210668 A1 | 12/2017 |
| WO | 2017211272 A1 | 12/2017 |
| WO | 2017216177 A1 | 12/2017 |
| WO | 2018059331 A1 | 4/2018 |
| WO | 2018103624 A1 | 6/2018 |
| WO | 2019109934 A1 | 6/2019 |
| WO | 2019109937 A1 | 6/2019 |
| WO | 2019134510 A1 | 7/2019 |
| WO | 2019148047 A1 | 8/2019 |
| WO | 2019219019 A1 | 11/2019 |
| WO | 2020034912 A1 | 2/2020 |

OTHER PUBLICATIONS

International Preliminary Report on Patentability for International Application No. PCT/US2020/045482, dated Feb. 17, 2022, 9 Pages.

International Search Report and Written Opinion for International Application No. PCT/US2020/039581, dated Nov. 20, 2020, 12 pages.

International Search Report and Written Opinion for International Application No. PCT/US2020/045482, dated Nov. 23, 2020, 9 Pages.

Jordan, et al., "Opioids and Their Complicated Receptor Complexes," Neuropsychopharmacology, Oct. 2000, vol. 23, pp. S5-S18, especially p. S6, col. 1, para 3.

Law P-Y., et al., "Molecular Mechanisms and Regulation of Opioid Receptor Signaling," Annual Review of Pharmacology and Toxicology, 2000, vol. 40, pp. 389-430.

Mannekens, et al., "Synthesis of the Diastereomers of Beta-Me-Tyr and Beta-Me-Phe and their Effect on the Biological Properties of the Delta Opioid receptor antagonist TIPP," Letters in Peptide Science, 1995, vol. 2, pp. 190-192.

Negus S.S., et al., "Effects of Peripherally Restricted Kappa Opioid Receptor Agonists on Pain-Related Stimulation and Depression of Behavior in Rats," The Journal of Pharmacology And Experimental Therapeutics, 2012, vol. 340, No. 3, pp. 501-509.

Non-Final Office Action for U.S. Appl. No. 16/988,229 dated Jan. 24, 2022, 14 pages.

Pommie C., et al., "IMGT Standardized Criteria for Statistical Analysis of Immunoglobulin V-REGION Amino Acid Properties," Journal of Molecular Recognition, 2004, vol. 17, pp. 17-32.

PubChem CID: 10877239, Create Date: Oct. 26, 2006 (Oct. 26, 2006), p. 2 Formula.

PubChem CID 11029875, Create Date: Oct. 26, 2006 (Oct. 26, 2006), p. 2, Formula.

Schrier A.J., et al., "New Chemical Entities Entering Phase III Trials in 2015," Chapter 24, Medicinal Chemistry Reviews, 2016, vol. 51, pp. 419-436.

Wadenberg M-L.G., "A Review of the Properties of Spiradoline: A Potent and Selective K-Opioid Receptor Agonist," CNS Drug Reviews, Summer, 2003, vol. 9, No. 2, pp. 187-198.

Walsh S.L., et al., "Enadoline, A Selective Kappa Opioid Agonist: Comparison with Butorphanol and Hydromorphone in Humans," Psychopharmacology, 2001, vol. 157, pp. 151-162.

\* cited by examiner

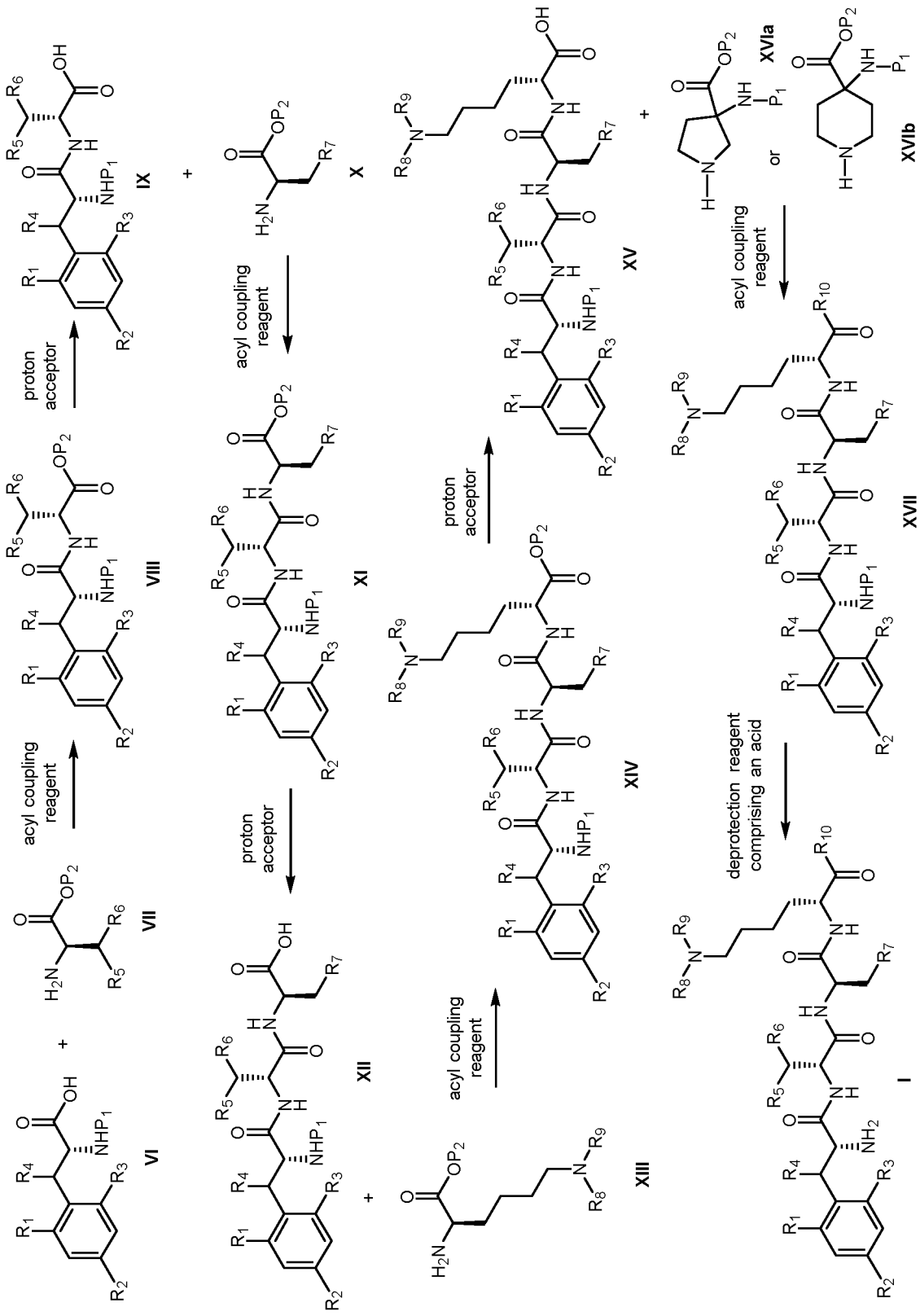

PEPTIDES FOR TREATMENT OF MEDICAL DISORDERS

FIELD OF THE INVENTION

The present disclosure generally relates to compounds which are selective kappa-opioid receptor agonist, method of preparation of these compounds, compositions that comprise these compounds, and methods for treating kappa-opioid receptor agonist related medical disorders.

BACKGROUND OF THE INVENTION

Opioid kappa receptors (KORs) are expressed in many parts of the body such as brain, spinal cord, and on central and peripheral terminals. KORs play an important role in signal transduction to maintain many physiological functions of the body. Like opioid mu receptors (MORs) and delta receptors (DORs), activation of KORs by agonist ligands leads to the inhibition of adenylyl cyclase and calcium channel activity while stimulation of the potassium channel activities (Law P Y, Wong Y H, Loh H H. Molecular mechanisms and regulation of opioid receptor signaling. Annu Rev Pharmacol Toxicol 2000; 40: 389-430).

Many physiological processes are related to the activation of KORs including analgesia, anti-pruritic actives (Inan S, Cowan A. Kappa opioid agonists suppress chloroquine-induced scratching in mice. Eur J. Pharmacol 2004; 502, 233-7), diuresis (Barber A, Gottschlich R. Novel developments with selective non-peptidic kappa-opioid receptor agonists. Exp Opinion Investigational drugs. 1997; 6: 1351-68; DeHaven-Hudkins D L, Dolls R E. Peripherally restricted opioid agonists are novel analgesic agents (Curr Pharm Des 2004; 10:743-57), inflammation agents, immune system modulation agents, etc. The agonists offer great potentials for KORs selective ligands to treat various medical disorder such as pain, depression, autoimmune disorders and neurological diseases. (Tyler C. Beck, Matthew A. Hapstack, Kyle R. Beck, and Thomas A. Dix. "Therapeutic Potential of Kappa Opioid Agonists", Pharmaceuticals (Basel). 2019 June; 12(2): 95).

Many KORs selective agonists were synthesized and evaluated as potential analgesics which are in avoid of side effects associated with traditional opioid analgesics like respiratory depression, dependence, addiction, and constipation; a few of them had already been tested in clinical trial but failed due to side effects like diuresis, sedation, and dysphoria, et al or lack of efficacy; examples include spiradoline mesylate (U62,066E) (Wadenberg M L, A review of the properties of spiradoline: a potent and selective kappa-opioid receptor agonist. CNS Drug Rev. 2003, Summer, 9(2): 187-98), enadoline for potential analgesics (Walsh S L., Strain E C, Abreu M. E. Bigelow G. E. Enadoline, a selective kappa opioid agonist: comparison with butorphanol and hydromorphone in humans. Psychopharmacology 2001, 157, 151-162) and ADL-10-0101 et al.

TRK-820 (Nalfurafine) was originally developed as potential analgesics but achieved success as anti-pruritic reagents and got regulatorily approved in Japan with brand name Remitch.

Highly opioid kappa-receptor selective and potent D-amino acids tetrapeptide agonists were reported by Ferring B V(US005965701A) and were further developed by Cara therapeutics. The lead tetrapeptide compound, CR-845, is currently under development by Cara therapeutics in the clinical trials as analgesics and anti-pruritic agents (Hesselink, J. M. K. CR845 (Difelikefalin), A Kappa Receptors Agonist in Phase III by CARA Therapeutics: A Case of 'Spin' in Scientific Writing? J. Pharm.& clinical Res. 2017 2(3), 001). Encouraged by the progress of CR-845 in clinical trial, several pharmaceutical companies also actively engaged in the discovery of peptide-based KORs selective agonist ligands via modifying molecular structure of CR-845 with hope to find new analgesics and potential anti-pruritus agents without conventional side effects of morphinan analgesics (CN107098871, WO2017211272A1, WO2018103624A1, WO2017210668A1, WO2018059331A1).

In addition, KORs agonists are also developed for other indications; for example, both fedotozine and asimadoline were tested as potential therapeutics for irritable bowel syndrome and dyspepsia.

What is needed is a novel kappa-opiate agonist that treats a variety of medical disorders.

FIGURES

FIG. 1 is a chemical reaction scheme useful to prepare the compound comprising Formula (I) in accordance with embodiments of the disclosure.

SUMMARY OF THE INVENTION

In one aspect, disclosed herein, are compounds comprising Formula (I) or a pharmaceutically acceptable salt thereof:

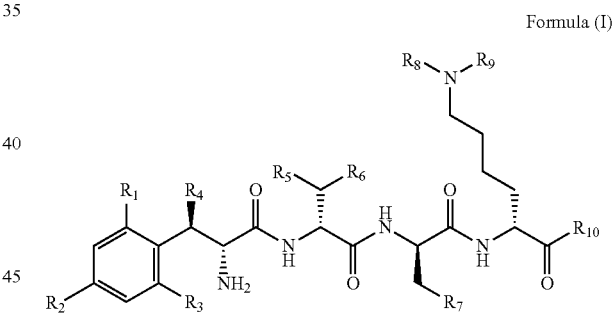

Formula (I)

wherein:

$R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;

$R_4$ and $R_7$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;

$R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl; unsubstituted aryl, substituted aryl, unsubstituted heterocyclic, or substituted heterocyclic;

$R_8$ and $R_9$ are independently selected from a group consisting of H, $C_1$-$C_8$ unsubstituted alkyl, $C_1$-$C_8$ substituted alkyl, O-substituted $C_1$-$C_8$ alkyl, O-unsubstituted $C_1$-$C_8$ alkyl, or $(OCH_2CH_2O)_n$;

$R_{10}$ is selected from a group consisting of

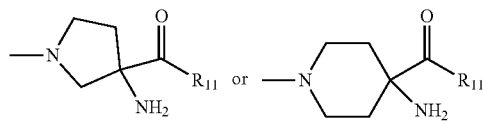

$R_{11}$ is selected from a group consisting of $OR_{12}$, or $NR_{13}R_{14}$;

$R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl, or $(OCH_2CH_2O)_n$;

$R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl, or $(OCH_2CH_2O)_n$; and n is an integer from 1 to 100.

In another aspect, disclosed herein, are methods of preparing the compound of Formula (I) or an acceptable pharmaceutical salt thereof:

Formula (I)

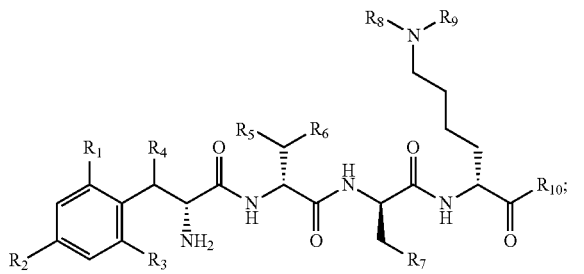

the method comprises:

a) contacting the compound comprising Formula (VI):

Formula (VI)

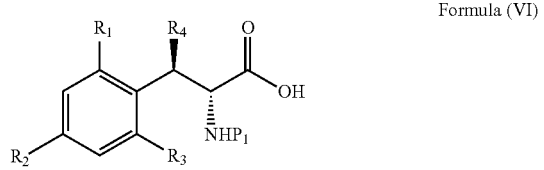

with the compound comprising Formula (VII):

Formula (VII)

in the presence of an acyl coupling reagent to form the compound comprising Formula (VIII):

Formula (VIII)

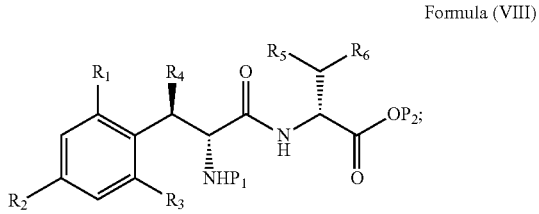

b) contacting the compound comprising Formula (VIII) with a proton acceptor to form the compound comprising Formula (IX):

Formula (IX)

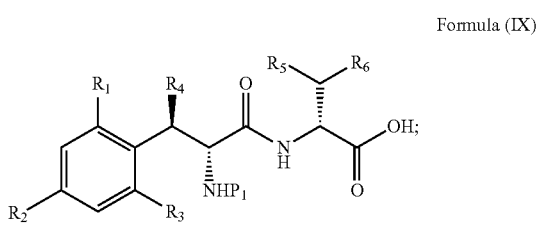

c) contacting the compound comprising Formula (IX) with the compound comprising Formula (X):

Formula (X)

in the presence of an acyl coupling reagent to form the compound comprising Formula (XI):

Formula (XI)

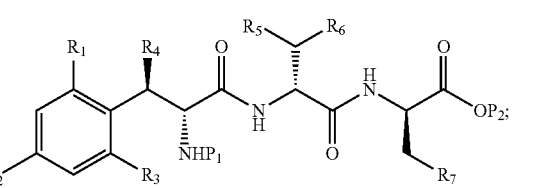

d) contacting the compound comprising Formula (XI) with a proton acceptor to form the compound comprising Formula (XII):

Formula (XII)

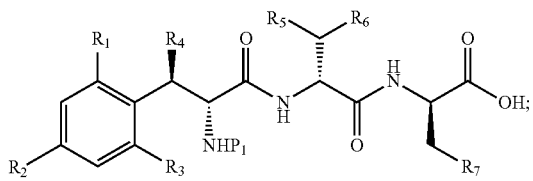

e) contacting the compound comprising Formula (XII) with the compound comprising Formula (XIII):

Formula (XIII)

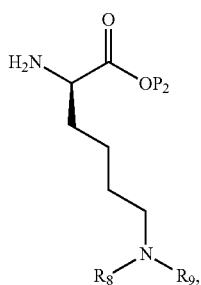

in the presence on an acyl coupling reagent to form the compound comprising Formula (XIV):

Formula (XIV)

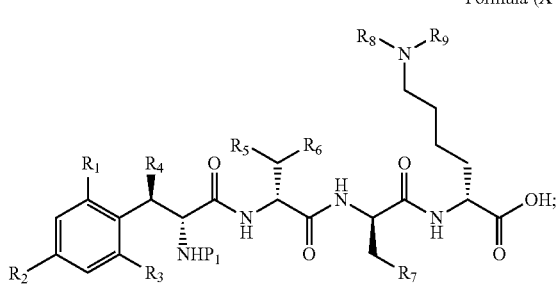

f) contacting the compound comprising Formula (XIV) with a proton acceptor to form the compound comprising Formula (XV):

Formula (XV)

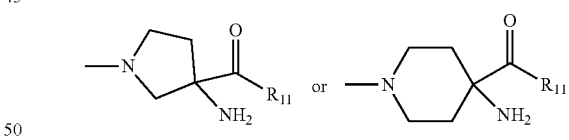

g) contacting the compound comprising Formula (XV) with the compound comprising Formula (XVI) in the presence of an acyl coupling reagent to form the compound comprising Formula (XVII):

Formula (XVII)

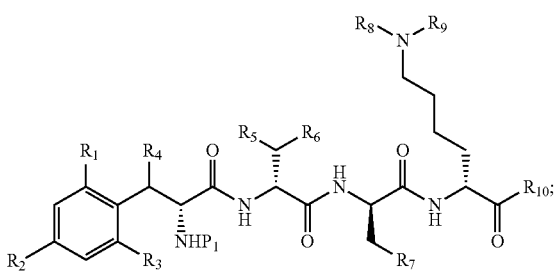

and
h) contacting the compound comprising Formula (XVII) with a deprotection reagent comprising an acid to form the compound comprising Formula (I);
wherein:
$R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;
$R_4$ and $R_7$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;
$R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl; unsubstituted aryl, substituted aryl, unsubstituted heterocyclic, or substituted heterocyclic;
$R_8$ and $R_9$ are independently selected from a group consisting of H, $C_1$-$C_8$ unsubstituted alkyl, $C_1$-$C_8$ substituted alkyl, O-substituted $C_1$-$C_8$ alkyl, O-unsubstituted $C_1$-$C_8$ alkyl, or $(OCH_2CH_2O)_n$;
$R_{10}$ is selected from a group consisting of $R_{11}$ is selected from a group consisting of $OR_{12}$, or $NR_{13}R_{14}$;
$R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl, or $(OCH_2CH_2O)_n$;
$R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl, or $(OCH_2CH_2O)_n$; and
n is an integer from 1 to 100.

In still another aspect, disclosed herein, are pharmaceutical compositions comprising the compound comprising Formula (I).

In still another aspect, disclosed herein, are methods for treating opioid receptor agonist related medical disorders, the methods comprising administering the pharmaceutical composition comprising the compound comprising Formula (I) to a subject in need thereof.

Other features and iterations of the invention are described in more detail below.

DETAILED DESCRIPTION OF THE INVENTION

The present disclosure provides compounds comprising Formula (I) or a pharmaceutically acceptable salt thereof, methods for preparing the compound comprising Formula (I) or an acceptable pharmaceutical salt thereof, compounds comprising the compound comprising Formula (I), and methods for treating opiod receptor agonist related medical disorders.

(I) Compounds Comprising Formula (I) or an Acceptable Pharmaceutically Acceptable Salt Thereof.

In one aspect of the present disclosure encompasses the compounds comprising Formula (I) or a pharmaceutically acceptable salt thereof:

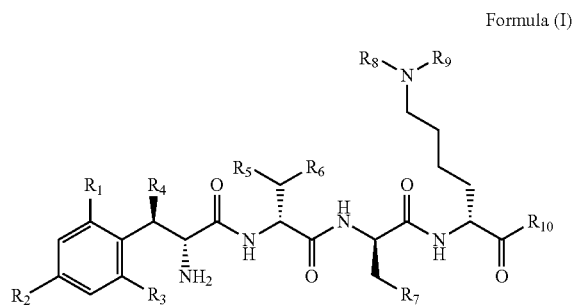

Formula (I)

wherein:
$R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;
$R_4$ and $R_7$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;
$R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, $C_3$-$C_{10}$ substituted cycloalkyl; unsubstituted aryl, substituted aryl, unsubstituted heterocyclic, or substituted heterocyclic;
$R_8$ and $R_9$ are independently selected from a group consisting of H, $C_1$-$C_8$ unsubstituted alkyl, $C_1$-$C_8$ substituted alkyl, O-substituted $C_1$-$C_8$ alkyl, O-unsubstituted $C_1$-$C_8$ alkyl, or $(OCH_2CH_2O)_n$;
$R_{10}$ is selected from a group consisting of:

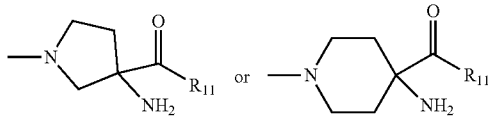

$R_{11}$ is selected from a group consisting of $OR_{12}$, or $NR_{13}R_{14}$;
$R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl, or $(OCH_2CH_2O)_n$;

$R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl, or $(OCH_2CH_2O)_n$; and
n is an integer from 1 to 100.

Generally, in accordance with embodiments, $R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl. In some embodiments, $R_1$, $R_2$, and $R_3$ are independently selected from a group consisting of H, CN, Cl, F, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In certain embodiments, $R_1$, $R_2$, and $R_3$ are independently selected from a group consisting of H, Cl, F, methyl, ethyl, propyl, or iso-propyl. In specific embodiments, $R_1$, $R_2$, and $R_3$ are H.

In general, in accordance with embodiments, $R_4$ and $R_7$ are independently selected from a group consisting of H, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In some embodiments, $R_4$ and $R_7$ are independently selected from a group consisting of H, methyl, ethyl, propyl, or iso-propyl. In specific embodiments, $R_4$ is methyl, and $R_7$ is iso-propyl.

Generally, in accordance with embodiments, $R_5$ and $R_6$ are independently selected from a group consisting of H, $C_1$-$C_4$ unsubstituted alkyl, $C_1$-$C_4$ substituted alkyl, $C_3$-$C_8$ unsubstituted cycloalkyl, $C_3$-$C_8$ substituted cycloalkyl, unsubstituted aryl, substituted aryl, unsubstituted heterocyclic; or substituted heterocyclic. In some embodiments, $R_5$ and $R_6$ are independently selected from a group consisting of H, methyl, ethyl, n-propyl, iso-propyl, cyclopropyl, cyclobutyl, cyclopentyl, cyclohexyl, or phenyl. In specific embodiment, $R_5$ is H and $R_6$ is phenyl.

In general, in accordance with embodiments, $R_8$ and $R_9$ are independently selected from a group consisting of H, $C_1$-$C_4$ unsubstituted alkyl, $C_1$-$C_4$ substituted alkyl, O-substituted $C_1$-$C_4$ alkyl, O-unsubstituted $C_1$-$C_4$ alkyl, or $(OCH_2CH_2O)_n$. In some embodiments, $R_8$ and $R_9$ are independently selected from a group consisting of H, methyl, ethyl, propyl, or iso-propyl. In specific embodiments, $R_8$ and $R_9$ are hydrogen.

Generally, with accordance with embodiments, $R_{10}$ is selected from a group consisting of

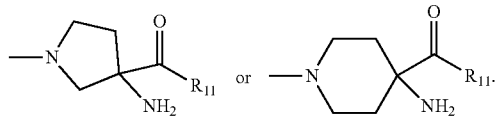

In general, in accordance with embodiments, $R_{11}$ is selected from a group consisting of $OR_{12}$, or $NR_{13}R_{14}$. In some embodiments, $R_{11}$ is selected from a group consisting of $OR_{12}$, or $NR_{13}R_{14}$. In specific embodiments, $R_{11}$ is $OR_{12}$.

Generally, in accordance with embodiments, $R_{12}$ is selected from a group consisting of H, $C_1$-$C_{12}$ unsubstituted alkyl, $C_1$-$C_{12}$ substituted alkyl, O-substituted $C_1$-$C_{12}$ alkyl, O-unsubstituted $C_1$-$C_{12}$ alkyl, or $(OCH_2CH_2O)_n$. In some embodiments, $R_{12}$ is selected from a group consisting of H, methyl, ethyl, n-propyl, or iso-propyl. In specific embodiments, $R_{12}$ is H or Me.

In general, in accordance with embodiments, $R_{13}$ and $R_{14}$ are independently selected from a group consisting of H, $C_1$-$C_{12}$ unsubstituted alkyl, $C_1$-$C_{12}$ substituted alkyl, O-substituted $C_1$-$C_{12}$ alkyl, O-unsubstituted $C_1$-$C_{12}$ alkyl, or $(OCH_2CH_2O)_n$. In some embodiments, $R_{13}$ and $R_{14}$ are independently selected from a group consisting of H, methyl, ethyl, n-propyl, iso-propyl, cyclopropyl, cyclobutyl, cyclopentyl, or cyclohexyl. In certain embodiments, $R_{13}$ and $R_{14}$, are absent Generally, in accordance with embodiments, n is an integer from 1 to 50. In some embodiments, n is an integer from 1 to 50. In certain embodiments, n is absent.

In one exemplary embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

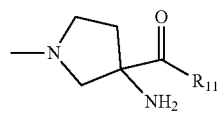

$R_{11}$ is $O1=112$; and $R_{12}$ is H; and $R_{13}$, $R_{14}$, and n are absent as shown in the compound comprising Formula (II):

Formula (II)

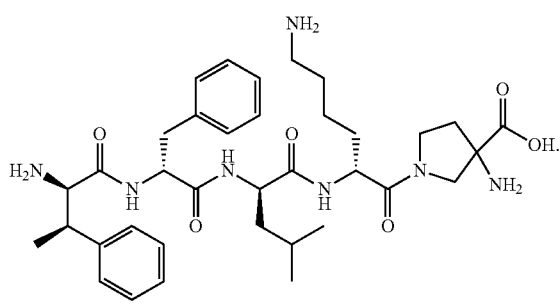

In another exemplary embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

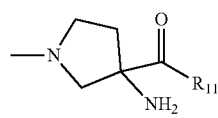

$R_{11}$ is $OR_{12}$; $R_{12}$ is Me; and $R_{13}$, $R_{14}$, and n are absent as shown in the compound comprising Formula (III):

Formula (III)

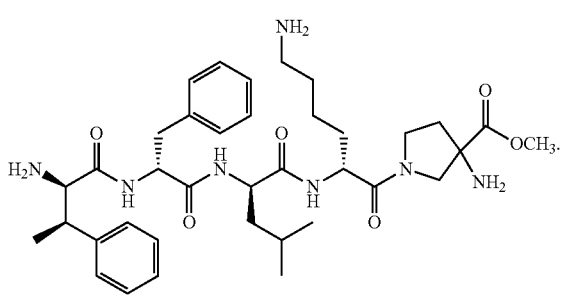

In still another exemplary embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

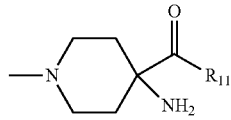

$R_{11}$ is $OR_{12}$; $R_{12}$ is H; and $R_{13}$, $R_{14}$, and n are absent as shown in the compound comprising Formula (IV):

Formula (IV)

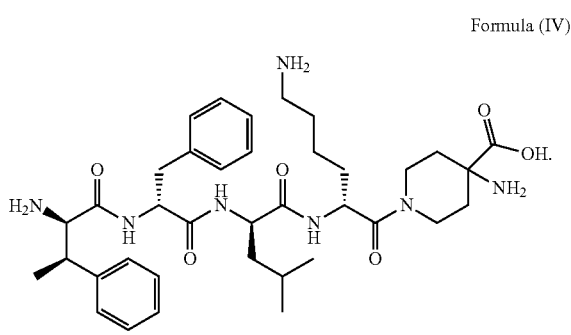 [SMILES: CC(C)C[C@@H](NC(=O)[C@@H](Cc1ccccc1)NC(=O)[C@H](N)[C@H](C)c1ccccc1)C(=O)N[C@H](CCCCN)C(=O)N1CCC(N)(C(=O)O)CC1]

In yet another exemplary embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

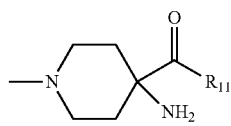

$R_{11}$ is $OR_{12}$; $R_{12}$ is Me; and $R_{13}R_{14}$, and n are absent as shown in the compound comprising Formula (V):

Formula (V)

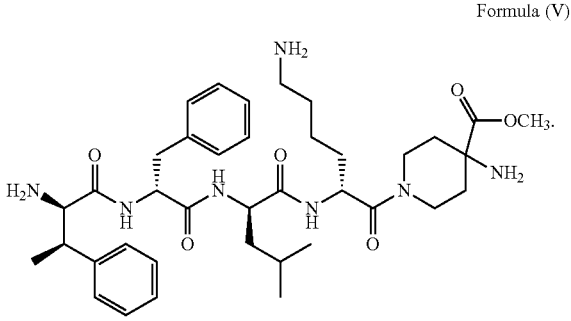 [SMILES: COC(=O)C1(N)CCN(C(=O)[C@@H](CCCCN)NC(=O)[C@@H](CC(C)C)NC(=O)[C@@H](Cc2ccccc2)NC(=O)[C@H](N)[C@H](C)c2ccccc2)CC1]

The compound comprising Formula (I) may be a free base or a salt. When the compound is in a salt form, the salt is preferably a pharmaceutically acceptable salt. Pharmaceutically acceptable salts may include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. In other embodiments, the pharmaceutically acceptable salt includes an alkaline or alkaline earth metal ion salt. In particular, sodium, potassium or other pharmaceutically acceptable inorganic salts are used. The salt forms may be amorphous or in various polymeric forms including hydrates, or solvates with alcohols or other solvents.

(II) Methods for Preparing the Compound Comprising Formula (I) or a Pharmaceutically Acceptable Salt Thereof.

In another aspect, the present disclosure encompasses methods of preparing the compound comprising Formula (I) or a pharmaceutically acceptable salt thereof:

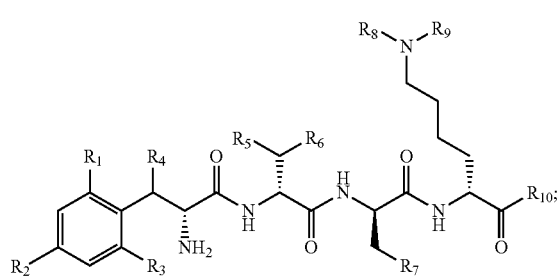

Formula (I)

the method comprises:

a) contacting the compound comprising Formula (VI):

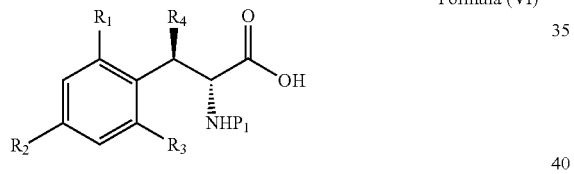

Formula (VI)

with the compound comprising Formula (VII):

Formula (VII)

in the presence of an acyl coupling reagent to form the compound comprising Formula (VIII):

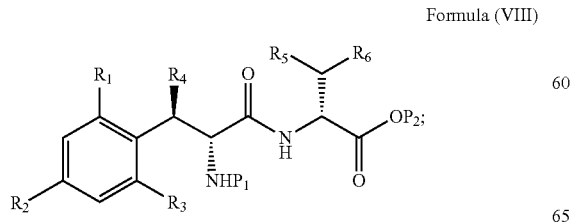

Formula (VIII)

b) contacting the compound comprising Formula (VIII) with a proton acceptor to form the compound comprising Formula (IX):

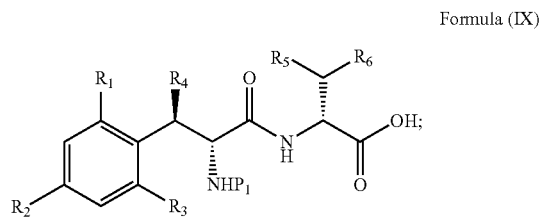

Formula (IX)

c) contacting the compound comprising Formula (IX) with the compound comprising Formula (X):

Formula (X)

in the presence of an acyl coupling reagent to form the compound comprising Formula (XI):

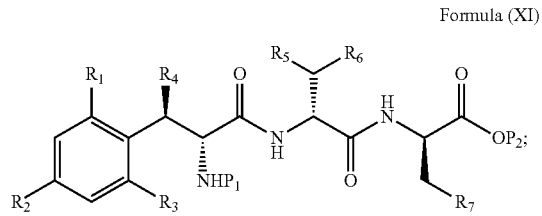

Formula (XI)

d) contacting the compound comprising Formula (XI) with a proton acceptor to form the compound comprising Formula (XII):

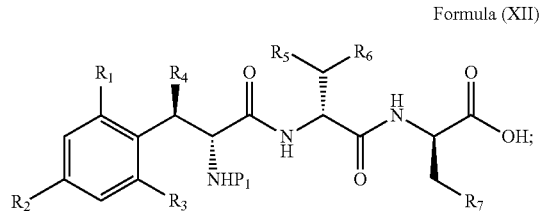

Formula (XII)

e) contacting the compound comprising Formula (XII) with the compound comprising Formula (XIII):

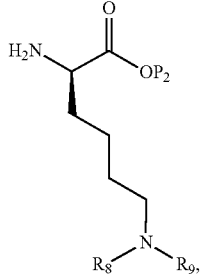

Formula (XIII)

in the presence on an acyl coupling reagent to form the compound comprising Formula (XIV):

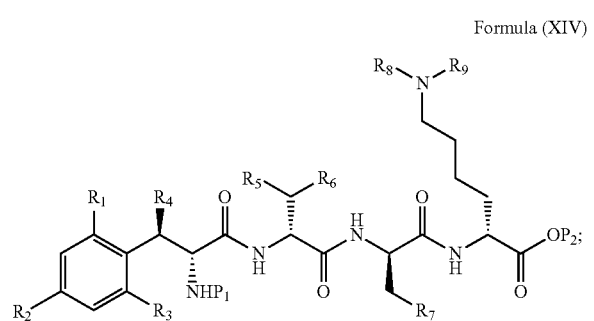

Formula (XIV)

f) contacting the compound comprising Formula (XIV) with a proton acceptor to form the compound comprising Formula (XV):

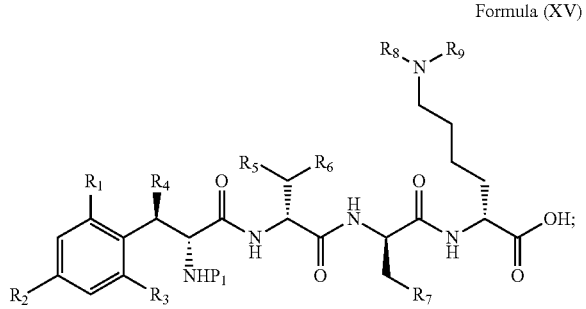

Formula (XV)

g) contacting the compound comprising Formula (XV) with the compound comprising Formula (XVI) in the presence of an acyl coupling reagent to form the compound comprising Formula (XVII):

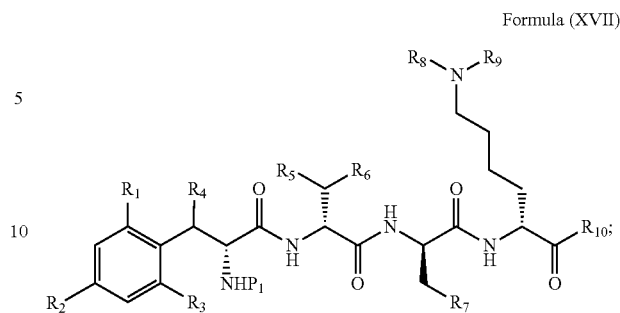

Formula (XVII)

and h) contacting the compound comprising Formula (XVII) with a deprotection reagent to form the compound comprising Formula (I) according to the Reaction Scheme depicted in FIG. 1;

wherein:

$R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;

$R_4$ and $R_7$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl;

$R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl; unsubstituted aryl, substituted aryl, unsubstituted heterocyclic, or substituted heterocyclic;

$R_8$ and $R_9$ are independently selected from a group consisting of H, $C_1$-$C_8$ unsubstituted alkyl, $C_1$-$C_8$ substituted alkyl, O-substituted $C_1$-$C_8$ alkyl, O-unsubstituted $C_1$-$C_8$ alkyl; $(OCH_2CH_2O)_n$;

$R_{10}$ is selected from a group consisting of

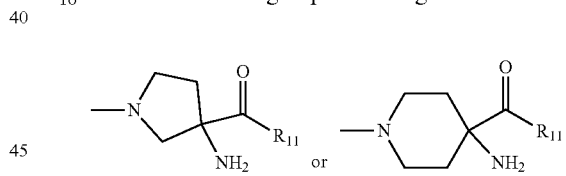

$R_{11}$ is selected from a group consisting of $OR_{12}$, or $NR_{13}R_{14}$;

$R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl; $(OCH_2CH_2O)_n$;

$R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, O-unsubstituted $C_1$-$C_{24}$ alkyl; $(OCH_2CH_2O)_n$;

n is an integer from 1 to 100;

$P_1$ is a nitrogen protecting group; and $P_2$ is a carboxylic acid protecting group.

Generally, according to the Reaction Schemes depicted in FIG. 1, $R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, or $C_3$-$C_{10}$ substituted cycloalkyl. In some embodiments, $R_1$, $R_2$, and $R_3$ are independently selected from a group consisting of H, CN, Cl, F, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In certain embodiments, $R_1$, $R_2$, and $R_3$ are independently selected from a group consisting of H, Cl, F, methyl, ethyl, propyl, or iso-propyl. In specific embodiments, $R_1$, $R_2$, and $R_3$ are H.

In general, according to the Reaction Schemes depicted in FIG. 1, $R_4$ and $R_7$ are independently selected from a group consisting of H, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In some embodiments, $R_4$ and $R_7$ are independently selected from a group consisting of H, methyl, ethyl, propyl, or iso-propyl. In specific embodiments, $R_4$ is methyl; and $R_7$ is iso-propyl.

Generally, according to the Reaction Schemes depicted in FIG. 1, $R_5$ and $R_6$ are independently selected from a group consisting of H, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl; unsubstituted aryl, substituted aryl, unsubstituted heterocyclic; or substituted heterocyclic. In some embodiments, $R_5$ and $R_6$ are independently selected from a group consisting of H, methyl, ethyl, n-propyl, iso-propyl, cyclopropyl, cyclobutyl, cyclopentyl, cyclohexyl, or phenyl. In specific embodiment, $R_5$ is H; and $R_6$ is phenyl.

In general, according to the Reaction Schemes depicted in FIG. 1, $R_8$ and $R_9$ are independently selected from a group consisting of H, $C_1$-$C_4$ unsubstituted alkyl, $C_1$-$C_4$ substituted alkyl, O-substituted $C_1$-$C_4$ alkyl, O-unsubstituted $C_1$-$C_4$ alkyl, or $(OCH_2CH_2O)_n$. In some embodiments, $R_8$ and $R_9$ are independently selected from a group consisting of H, methyl, ethyl, propyl, or iso-propyl. In specific embodiments, $R_8$ and $R_9$ are hydrogen.

Generally, according to the Reaction Schemes depicted in FIG. 1, $R_{10}$ is selected from a group consisting of

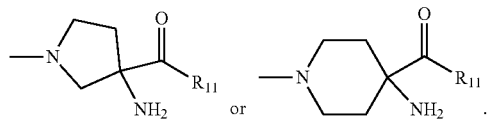

In general, in accordance with embodiments, $R_{11}$ is selected from a group consisting of $OR_{12}$, or $NR_{13}R_{14}$. In some embodiments, $R_{11}$ is selected from a group consisting of $OR_{12}$, or $NR_{13}R_{14}$. In specific embodiments, $R_{11}$ is $OR_{12}$.

Generally, according to the Reaction Schemes depicted in FIG. 1, $R_{12}$ is selected from a group consisting of H, $C_1$-$C_{12}$ unsubstituted alkyl, $C_1$-$C_{12}$ substituted alkyl, O-substituted $C_1$-$C_{12}$ alkyl, O-unsubstituted $C_1$-$C_{12}$ alkyl, or $(OCH_2CH_2O)_n$. In some embodiments, $R_{12}$ is selected from a group consisting of H, methyl, ethyl, n-propyl, iso-propyl. In specific embodiments, $R_{12}$ is H or Me.

In general, according to the Reaction Schemes depicted in FIG. 1, $R_{13}$ and $R_{14}$ are independently selected from a group consisting of H, $C_1$-$C_{12}$ unsubstituted alkyl, $C_1$-$C_{12}$ substituted alkyl, O-substituted $C_1$-$C_{12}$ alkyl, O-unsubstituted $C_1$-$C_{12}$ alkyl; $(OCH_2CH_2O)_n$. In some embodiments, $R_{13}$ and $R_{14}$ are independently selected from a group consisting of H, methyl, ethyl, n-propyl, iso-propyl, cyclopropyl, cyclobutyl, cyclopentyl, or cyclohexyl. In certain embodiments, $R_{13}$ and $R_{14}$, are absent.

Generally, according to the Reaction Schemes depicted in FIG. 1, n is an integer from 1 to 50. In some embodiments, n is an integer from 1 to 50. In certain embodiments, n is absent.

In general, in accordance with embodiments of the Reaction Scheme depicted in FIG. 1, $P_1$ is a suitable nitrogen protecting group. The nitrogen protecting group comprises a carbamate. Non-limiting examples of these protecting groups may be tert butyloxycarbonyl carbamate (BOC), 9-fluorenylmethyl carbamate (FMOC), benzyl carbamate (CBZ), and alike. Suitable nitrogen protecting groups, methods for attaching these protecting groups, and method for removing these protecting groups are described, for example, in "Protective Groups in Organic Synthesis" by T. W. Greene, John Wiley & Sons, 2006. In specific embodiments, $P_1$ is BOC.

Generally, in accordance with embodiments of the Reaction Scheme depicted in FIG. 1, $P_2$ is a suitable carboxylic acid protecting group. The carboxylic acid (carboxy) protecting group comprises an ester, an amide, or a hydrazide. Non-limiting examples of carboxylic acid protecting groups may be methyl ester, ethyl ester, benzyl ester, N, N-dimethyl amide, N-phenyl hydrazide, or alike. Suitable carboxylic acid protecting groups, methods for attaching these protecting groups, and method for removing these protecting groups are described, for example, in "Protective Groups in Organic Synthesis" by T. W. Greene, John Wiley & Sons, 2006. In specific embodiments, $P_2$ is a methyl group.

In one preferred embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

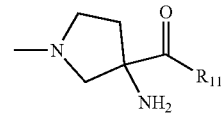

$R_{11}$ is $OR_{12}$; and $R_{12}$ is H; and $R_{13}$, $R_{14}$, and n are absent as shown in the compound comprising Formula (II):

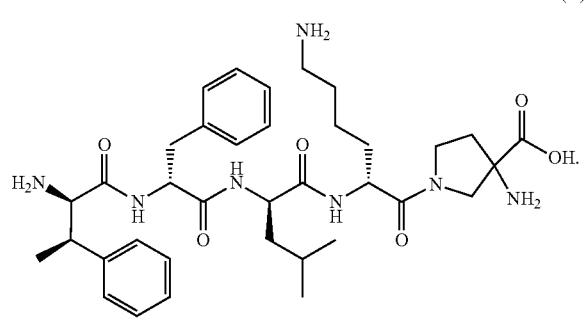

Formula (II)

In another preferred embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

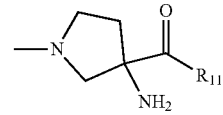

$R_{11}$ is $OR_{12}$; $R_{12}$ is Me; and $R_{13}$, $R_{14}$, and n are absent as shown in the compound comprising Formula (III):

Formula (III)

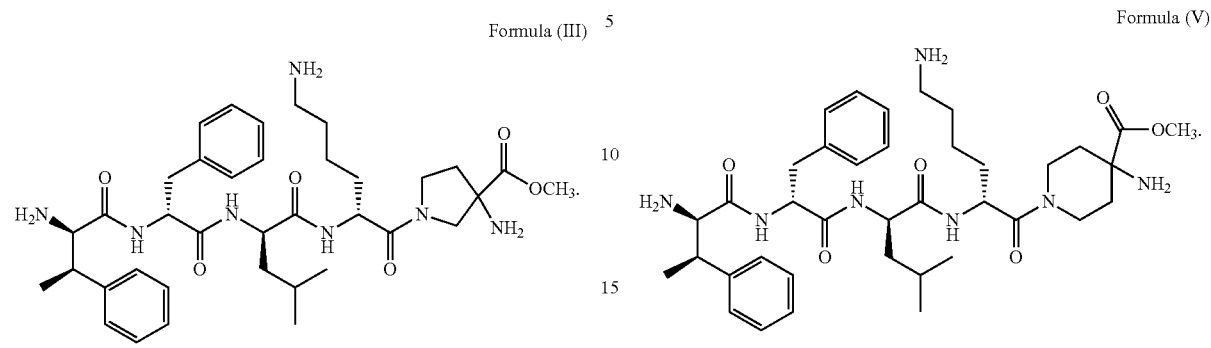

In still another preferred embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

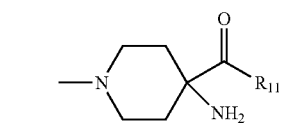

$R_{11}$ is $OR_{12}$; $R_{12}$ is H; and $R_{13}$, $R_{14}$, and n are absent as shown in the compound comprising Formula (IV):

Formula (IV)

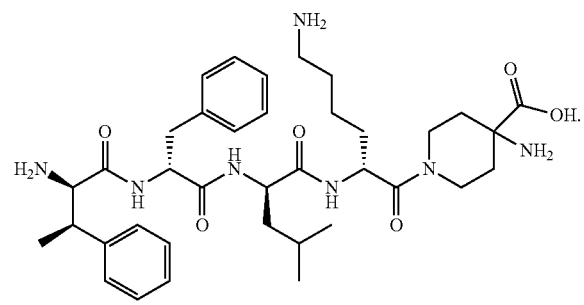

In yet another preferred embodiment, $R_1$, $R_2$, $R_3$, $R_5$, $R_8$, and $R_9$ are H; $R_4$ is methyl; $R_6$ is phenyl; $R_7$ is iso-propyl; $R_{10}$ is

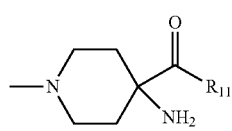

$R_{11}$ is $OR_{12}$; $R_{12}$ is Me; and $R_{13}$, $R_{14}$, and n are absent as shown in the compound comprising Formula (V):

Formula (V)

Step (a)

As discussed above, Step (a) of the eight step methods involves contacting the compound comprising Formula (VI) with the compound comprising Formula (VII) in the presence an acyl coupling reagent to form a reaction mixture. After work-up and isolation, the compound comprising Formula (VIII) is isolated. This method step is termed a "peptide coupling" or an "acyl coupling."

The compound comprising Formula (VI) as depicted in FIG. 1 is detailed above. In some embodiments, $R_1$, $R_2$, and $R_3$ are independently selected from a group consisting of H, CN, Cl, F, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In certain embodiments, $R_1$, $R_2$, and $R_3$ are independently selected from a group consisting of H, Cl, F, methyl, ethyl, propyl, or iso-propyl. In specific embodiments, $R_1$, $R_2$, and $R_3$ are H.

In some embodiments, $R_4$ is independently selected from a group consisting of H, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In certain embodiments, $R_4$ is selected from a group consisting of H, methyl, ethyl, propyl, or iso-propyl. In specific embodiments, $R_4$ is methyl.

In some embodiments, $P_1$ is a nitrogen protecting group. In specific embodiments, $P_1$ is a BOC group. In one preferred embodiment, the compound comprising Formula (VI) is (2R,3R)—BOC-beta-methyl-phenylalanine.

The compound comprising Formula (VII) as depicted in FIG. 1 is detailed above. In some embodiments, $R_5$ and $R_6$ are independently selected from a group consisting of H, $C_1$-$C_4$ unsubstituted alkyl, $C_1$-$C_4$ substituted alkyl, $C_3$-$C_8$ unsubstituted cycloalkyl, $C_3$-$C_8$ substituted cycloalkyl, unsubstituted aryl, substituted aryl, unsubstituted heterocyclic, or substituted heterocyclic. In certain embodiments, $R_5$ and $R_6$ are independently selected from a group consisting of H, methyl, ethyl, n-propyl, iso-propyl, cyclopropyl, cyclobutyl, cyclopentyl, cyclohexyl, or phenyl. In specific embodiments, $R_5$ is H and $R_6$ is phenyl.

In some embodiments, $P_2$ is a carboxylic acid protecting group. In specific embodiments, $P_2$ is a methyl group. In one preferred embodiment, the compound comprising Formula (VII) is D-phenylalanine methyl ester hydrochloride.

Generally, the equivalent ratio of the comprising Formula (VI) to the compound comprising Formula (VII) may range from about 1.0:1.0 to about 1.0:1.5. In various embodiments, equivalent ratio of the comprising Formula (VI) to the compound comprising Formula (VII) may range from about 1.0:1.0 to about 1.0:1.5, from about 1.0:1.0 to about 1.0:1.3, or from about 1.0:1.0 to about 1.0:1.2. In one preferred embodiment, equivalent ratio of the comprising Formula (VI) to the compound comprising Formula (VII) may be about 1:0:1.1.

Step (a) of the method utilizes an acyl coupling reagent. The acyl coupling reagent converts the carboxylic acid portion of the compound comprising formula (VI) into an activated acyl compound. Non-limiting examples of acyl coupling reagent include trifluoromethanesulfonic anhydride, p-toluenesulfonyl anhydride, methanesulfonic anhydride, thionyl chloride, oxalyl chloride, sulfuryl chloride, phosphorus oxychloride, phosphorus pentachloride, carbodiimides (such as: N, N'-dicyclohexylcarbodiimide, 1,1'-carbonyldipiperidine, N, N'-diisopropylcarbodiimide, 1-ethyl-3-(3-dimethylaminopropyl) carbodiimide), 1,1'-carbonyldiimidazole, 1,1'-carbonyldtriazole, cyanuric chloride, 2,4-dichloro-6-methoxy-1,3,5-triazine, 2-chloro-4,6-dimethoxy-1,3,5-triazine, ethyl chloroformate, isobutyl chloroformate, acetic anhydride, trichloroacetic anhydride, or trifluoroacetic anhydride. In various embodiments, an additional activation agent may be added. Non-limiting examples of additional activation agents may include 1-hydroxybenzotriazole, N-hydroxysuccinimide, or N-hydroxyphthalamide. In one preferred embodiment, the acyl coupling reagent may be 1-ethyl-3-(3-dimethylaminopropyl) carbodiimide) or a salt thereof.

Generally, the equivalent ratio of the comprising Formula (VI) to the acyl coupling reagent may range from about 1.0:1.0 to about 1.0:1.5. In various embodiments, equivalent ratio of the comprising Formula (VI) to the acyl coupling reagent may range from about 1.0:1.0 to about 1.0:1.5, from about 1.0:1.0 to about 1.0:1.3, or from about 1.0:1.2. In one preferred embodiment, equivalent ratio of the comprising Formula (VI) to the acyl coupling reagent may be about 1:0:1.1.

Step (a) further comprises a proton acceptor. The proton acceptor will vary depending on the starting substrate, the acyl coupling reagent, and the reaction conditions. The proton acceptor may be inorganic or organic in nature. Non-limiting examples of suitable inorganic proton acceptors include sodium hydroxide, potassium hydroxide, calcium hydroxide, barium hydroxide, cesium carbonate, sodium bicarbonate, potassium bicarbonate, sodium carbonate, potassium carbonate, sodium borate, sodium dihydrogen phosphate, disodium hydrogen phosphate, sodium methoxide, sodium tert-butoxide, potassium tert-butoxide, sodium acetate, and potassium acetate. The proton acceptor may be an amine. The organic proton acceptor may be a secondary amine, a tertiary amine, or combinations thereof. The amine may be chiral or achiral. Non-limiting examples of suitable secondary amines include ethyl methyl amine, dimethyl amine, diethyl amine, dicyclohexyl amine, methyl cyclohexyl amine, phenyl ethyl amine, dibenzyl amine, methyl benzyl amine, ethyl benzyl amine, cyclohexyl phenyl amine, dibutyl amine, ditertiarybutyl amine, dipropyl amine, dipentylamine, dicyclohexyl amine, piperidine, 2-methylpiperidine, 2,5-dimethylpiperidine, 2,6-dimethylpiperidine, piperazine, 2-methylpiperazine, 2,6-dimethylpiperazine, and morpholine. Non-limiting examples of suitable tertiary amines include trimethylamine, triethylamine, diisopropylethylamine, tripropylamine, tributylamine, 4-methylmorpholine, 4-ethylmorpholine, N-methylpyrrolidine, N-methylpiperidine, 1,8-diazabicyclo[5.4.0]undec-7-ene (DBU), pyrazine, 4-dimethylaminopyridine, pyridine, and 2,6-lutidine. Non-limiting examples of chiral secondary amines (R)-α-methylbenzylamine, (S)-α-methylbenzylamine, (R)-α,α-diphenyl-2-pyrrolidinemethanol (DPP), (S)-α,α-diphenyl-2-pyrrolidinemethanol (DPP), (R)-α,α-diphenyl-2-pyrrolidinemethanol trimethylsilyl ether (DPPT) and (S)-α,α-diphenyl-2-pyrrolidinemethanol trimethylsilyl ether (DPPT). In one preferred embodiment, the proton acceptor is 4-methylmorpholine (N-methylmorpholine).

Generally, the equivalent ratio of the comprising Formula (VI) to the proton acceptor may range from about 1.0:1.0 to about 1.0:2.5. In various embodiments, equivalent ratio of the comprising Formula (VI) to the proton acceptor may range from about 1.0:1.0 to about 1.0:2.5, from about 1.0:1.0 to about 1.0:2.25, or from about 1.0:2.2. In one preferred embodiment, equivalent ratio of the comprising Formula (VI) to the proton acceptor may be about 1:0:2.1.

Step (a), as detailed herein, comprise a solvent. As recognized by those of skill in the art, the solvent can and will vary depending on the starting substrates in the process. The solvent may be a polar protic solvent, a polar aprotic solvent, a non-polar solvent, or combinations thereof. Suitable examples of polar protic solvents include, but are not limited to, water; alcohols such as methanol, ethanol, isopropanol, n-propanol, iso-butanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof. In preferred embodiment, the solvent may be dimethylformamide.

In general, the volume to weight ratio of the solvent to the compound comprising Formula (VI) will range from about 0.5:1 to about 500:1. In various embodiments, the volume to weight ratio of the solvent to the compound comprising Formula (VI) may range from about 0.5:1 to about 500:1, from about 2:1 to about 250:1, from about 5:1 to about 200:1, or from about 10:1 to about 50:1. In an exemplary embodiment, the volume to weight ratio of the solvent to the compound comprising Formula (VI) may range from about 12:1 to about 20:1.

In general, the reaction of Step (a) will be conducted at a temperature that ranges from about −20° C. to about 25° C. depending on the solvent utilized. In various embodiments, the temperature of the reaction may range from about −20° C. to about 25° C., from about −10° C. to about 20° C., or from about −5° C. to about 5° C. In one embodiment, the reaction may be conducted at temperature about 0° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 2 hours. In some embodiments, the duration of the reaction may range from about 5 minutes to about 30 minutes, from about 30 minutes to about 1 hours, or from about 1 hour to about 2 hours. In an exemplary embodiment, the reaction may be allowed to proceed for about 1 hour. In this context, a "completed reaction" generally means that the reaction mixture contains a significantly diminished amount of the compound of Formula (VI). Typically, the amount of the compound of Formula (VI) remaining in the reaction mixture at the end of the reaction may be less than about 10%, less than about 5%, or less than about 2%.

The compound comprising Formula (VIII) may have a yield of at least about 60%. In various embodiments, the compound comprising Formula (VIII) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (VIII) may have a yield of about 90%.

Step (b)

Step (b) of the eight step method involves contacting the compound comprising Formula (VIII) with a proton acceptor forming a reaction mixture. Upon work-up and isolation, the compound comprising Formula (IX) is obtained. This method step is termed a "deprotection" reaction.

The compound comprising Formula (VIII) is described in more detail above.

Suitable proton acceptors are detailed above in Section (II)(a). In one preferred embodiment, the proton acceptor is NaOH.

Generally, the equivalent ratio of the comprising Formula (VIII) to the proton acceptor may range from about 1.0:1.0 to about 1.0:5.0. In various embodiments, equivalent ratio of the comprising Formula (VIII) to the proton acceptor may range from about 1.0:1.0 to about 1.0:5.0, from about 1.0:1.0 to about 1.0:3.0, or from about 1.0:1.5. In one preferred embodiment, equivalent ratio of the comprising Formula (VIII) to the proton acceptor may be about 1:0.2.0.

Step (b) further comprises a solvent. Suitable solvents are detailed above in Section (II)(a). In one preferred embodiment, the solvent is a combination of methanol and water.

In general, the volume to weight ratio of the solvent to the compound comprising Formula (VI) will range from about 0.5:1 to about 500:1. In various embodiments, the volume to weight ratio of the solvent to the compound comprising Formula (VI) may range from about 0.5:1 to about 500:1, from about 5:1 to about 200:1, from about 10:1 to about 100:1, or from about 15:1 to about 50:1. In preferred embodiment, the volume to weight ratio of the solvent to the compound comprising Formula (VIII) may be about 20:1.

In general, the reaction of Step (b) will be conducted at a temperature that ranges from about 0° C. to about 50° C. depending on the solvent utilized. In various embodiments, the temperature of the reaction may range from about 0° C. to about 50° C., from about 10° C. to about 40° C., or from about 20° C. to about 30° C. In one embodiment, the reaction may be conducted at temperature about 23° C. (room temperature). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 30 minutes to about 4 hours. In some embodiments, the duration of the reaction may range from about 30 minutes to about 1 hour, from about 1 hour to about 2 hours, or from about 2 hours to about 4 hours. In a preferred embodiment, the reaction may be allowed to proceed for about 2 hour. In this context, a "completed reaction" generally means that the reaction mixture contains a significantly diminished amount of the compound of Formula (VIII). Typically, the amount of the compound of Formula (VIII) remaining in the reaction mixture at the end of the reaction may be less than about 10%, less than about 5%, or less than about 2%.

After the completion of Step (b), the pH of the reaction mixture is adjusted to a pH of less than about 6.0. In various embodiments, the pH is adjusted to less than about pH 6.0, less than about pH 5.0, less than about pH 4.0, less than about pH 3.0, less than about pH 2.0, or less than about pH 1.0. In one preferred embodiment, the pH is adjusted to a range from about pH 2.0 to a pH of about 2.5.

This pH adjustment uses an aqueous acid. Non-limiting examples of suitable acids may be HCl, $H_2SO_4$, acetic acid, methanesulfonic acid, or similar organic or inorganic acids. In one preferred embodiment, the useful acid is HCl.

The compound comprising Formula (IX) may have a yield of at least about 60%. In various embodiments, the compound comprising Formula (IX) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (IX) may have a yield of about 95%.

Step (c)

Step (c) of the eight step process involves contacting the compound comprising Formula (IX) with the compound comprising Formula (X) in the presence of an acyl coupling reagent to form a reaction mixture. Upon work-up and isolation, the compound comprising Formula (XI) is obtained.

The compound comprising Formula (IX) is detailed above.

The compound comprising Formula (X) is detailed above. In some embodiments, $R_7$ is selected from a group consisting of H, $C_1$-$C_4$ unsubstituted alkyl, $C_1$-$C_4$ substituted alkyl, $C_3$-$C_8$ unsubstituted cycloalkyl, or $C_3$-$C_8$ substituted cycloalkyl. In certain embodiments, $R_7$ is selected from a group consisting of H, methyl, ethyl, propyl, or iso-propyl. In preferred embodiments, $R_7$ is iso-propyl.

In some embodiments, $P_2$ is a carboxylic acid protecting group. In specific embodiments, $P_2$ is a methyl group. In one preferred embodiment, the compound comprising Formula (X) is D-leucine methyl ester hydrochloride.

Generally, the equivalent ratio of the comprising Formula (IX) to the compound comprising Formula (X) may range from about 1.0:1.0 to about 1.0:1.5. In various embodiments, equivalent ratio of the comprising Formula (IX) to the compound comprising Formula (X) may range from about 1.0:1.0 to about 1.0:1.5, from about 1.0:1.0 to about 1.0:1.3, or from about 1.0:1.2. In one preferred embodiment, equivalent ratio of the comprising Formula (IX) to the compound comprising Formula (X) may be about 1:0:1.1.

The method of Step (c) utilizes an acyl coupling reagent and a proton acceptor. Suitable acyl coupling reagents and proton acceptors are detailed above in Section (II)(a). In one preferred embodiment, the acyl coupling reagent is 1-ethyl-3-(3-dimethylaminopropyl) carbodiimide) or a salt thereof and the proton acceptor is 4-methyl morpholine.

Generally, the equivalent ratio of the comprising Formula (IX) to the acyl coupling reagent may range from about 1.0:1.0 to about 1.0:1.5. In various embodiments, equivalent ratio of the comprising Formula (IX) to the acyl coupling reagent may range from about 1.0:1.0 to about 1.0:1.5, from about 1.0:1.0 to about 1.0:1.3, or from about 1.0:1.2. In one preferred embodiment, equivalent ratio of the comprising Formula (IX) to the acyl coupling reagent may be about 1:0:1.1.

Generally, the equivalent ratio of the comprising Formula (IX) to the proton acceptor may range from about 1.0:1.0 to about 1.0:2.5. In various embodiments, equivalent ratio of the comprising Formula (IX) to the proton acceptor may range from about 1.0:1.0 to about 1.0:2.5, from about 1.0:1.0 to about 1.0:2.25, or from about 1.0:2.2. In one preferred embodiment, equivalent ratio of the comprising Formula (IX) to the proton acceptor may be about 1:0:2.1.

Step (c) comprises a solvent. Suitable solvents are detailed above in Section (II)(a). In one preferred embodiment, the solvent useful in Step (c) is dimethylformamide.

In general, the volume to weight ratio of the solvent to the compound comprising Formula (IX) will range from about 0.5:1 to about 500:1. In various embodiments, the volume to weight ratio of the solvent to the compound comprising Formula (IX) may range from about 0.5:1 to about 500:1, from about 2:1 to about 250:1, from about 5:1 to about 200:1, or from about 10:1 to about 50:1. In an exemplary embodiment, the volume to weight ratio of the solvent to the compound comprising Formula (IX) may range from about 12:1 to about 20:1.

In general, the reaction of Step (c) will be conducted at a temperature that ranges from about −20° C. to about 25° C. depending on the solvent utilized. In various embodiments, the temperature of the reaction may range from about −20° C. to about 25° C., from about −10° C. to about 20° C., or from about −5° C. to about 5° C. In one embodiment, the reaction may be conducted at temperature about 0° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 2 hours. In some embodiments, the duration of the reaction may range from about 5 minutes to about 30 minutes, from about 30 minutes to about 1 hours, or from about 1 hour to about 2 hours. In a preferred embodiment, the reaction may be allowed to proceed for about 1 hour. In this context, a "completed reaction" generally means that the reaction mixture contains a significantly diminished amount of the compound of Formula (IX). Typically, the amount of the compound of Formula (IX) remaining in the reaction mixture at the end of the reaction may be less than about 10%, less than about 5%, or less than about 2%.

The compound comprising Formula (XI) may have a yield of at least about 60%. In various embodiments, the compound comprising Formula (XI) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (XI) may have a yield of about 96%.

Step (d)

Step (d) of the eight step method involves contacting the compound comprising Formula (XI) with a proton acceptor forming a reaction mixture. Upon work-up and isolation, the compound comprising Formula (XII) is obtained. This method step is termed a "deprotection" reaction.

The compound comprising Formula (XI) is described in more detail above.

Suitable proton acceptors are detailed above in Section (II)(b). In one preferred embodiment, the proton acceptor is NaOH or LiOH.

Generally, the equivalent ratio of the comprising Formula (XI) to the proton acceptor may range from about 1.0:1.0 to about 1.0:5.0. In various embodiments, equivalent ratio of the comprising Formula (XI) to the proton acceptor may range from about 1.0:1.0 to about 1.0:5.0, from about 1.0:1.0 to about 1.0:3.0, or from about 1.0:1.5. In one preferred embodiment, equivalent ratio of the comprising Formula (XI) to the proton acceptor may be about 1:0:2.0.

Step (d) further comprises a solvent. Suitable solvents are detailed above in Section (II)(b). In one preferred embodiment, the solvent is a combination of methanol and water.

In general, the volume to weight ratio of the solvent to the compound comprising Formula (XI) will range from about 0.5:1 to about 500:1. In various embodiments, the volume to weight ratio of the solvent to the compound comprising Formula (XI) may range from about 0.5:1 to about 500:1, from about 5:1 to about 200:1, from about 10:1 to about 100:1, or from about 15:1 to about 50:1. In preferred embodiment, the volume to weight ratio of the solvent to the compound comprising Formula (XI) may be about 20:1.

In general, the reaction of Step (d) will be conducted at a temperature that ranges from about 0° C. to about 50° C. depending on the solvent utilized. In various embodiments, the temperature of the reaction may range from about 0° C. to about 50° C., from about 10° C. to about 40° C., or from about 20° C. to about 30° C. In one embodiment, the reaction may be conducted at temperature about 23° C. (room temperature). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 30 minutes to about 4 hours. In some embodiments, the duration of the reaction may range from about 30 minutes to about 1 hour, from about 1 hour to about 2 hours, or from about 2 hours to about 4 hours. In a preferred embodiment, the reaction may be allowed to proceed for about 2 hour. In this context, a "completed reaction" generally means that the reaction mixture contains a significantly diminished amount of the compound of Formula (XI). Typically, the amount of the compound of Formula (XI) remaining in the reaction mixture at the end of the reaction may be less than about 10%, less than about 5%, or less than about 2%.

After the completion of Step (d), the pH of the reaction mixture is adjusted to a pH of less than about 6.0. In various embodiments, the pH is adjusted to less than about pH 6.0, less than about pH 5.0, less than about pH 4.0, less than about pH 3.0, less than about pH 2.0, or less than about pH 1.0. In one preferred embodiment, the pH is adjusted to a range from about pH 2.0 to a pH of about 2.5.

This pH adjustment uses an aqueous acid. Non-limiting examples of suitable acids may be HCl, $H_2SO_4$, acetic acid, methanesulfonic acid, or similar organic or inorganic acids. In one preferred embodiment, the useful acid is HCl.

The compound comprising Formula (XII) may have a yield of at least about 60%. In various embodiments, the compound comprising Formula (XII) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (XII) may have a yield of about 95%.

Step (e)

Step (e) of the eight step process involves contacting the compound comprising Formula (XII) with the compound comprising Formula (XIII) in the presence of an acyl coupling reagent to form a reaction mixture. Upon work-up and isolation, the compound comprising Formula (XIV) is obtained.

The compound comprising Formula (XII) is detailed above.

The compound comprising Formula (XIII) is detailed above. In some embodiments, $R_8$ and $R_9$ are independently selected from a group consisting of H, $C_1$-$C_4$ unsubstituted alkyl, $C_1$-$C_4$ substituted alkyl, O-substituted $C_1$-$C_4$ alkyl, 0-unsubstituted $C_1$-$C_4$ alkyl, $(OCH_2CH_2O)_n$, or a nitrogen protecting group ($P_1$). In certain embodiments, $R_8$ and $R_9$ are independently selected from a group consisting of H, methyl, ethyl, propyl, iso-propyl, or a nitrogen protecting group ($P_1$). In specific embodiments, $R_8$ and $R_9$ are independently selected from a group consisting of H and a nitrogen protecting group ($P_1$).

In some embodiments, n is an integer from 1 to 10. In specific embodiments, n is absent.

In some embodiments, $P_1$ is a nitrogen protecting group. In specific embodiments, $P_1$ is a BOC group.

In some embodiments, $P_2$ is a carboxylic acid protecting group. In specific embodiments, $P_2$ is a methyl group. In one preferred embodiment, the compound comprising Formula (XIII) is D-lysine methyl ester hydrochloride.

Generally, the equivalent ratio of the comprising Formula (XII) to the compound comprising Formula (XIII) may range from about 1.0:1.0 to about 1.0:1.5. In various embodiments, equivalent ratio of the comprising Formula (XII) to the compound comprising Formula (XIII) may range from about 1.0:1.0 to about 1.0:1.5, from about 1.0:1.0 to about 1.0:1.3, or from about 1.0:1.2. In one preferred embodiment, equivalent ratio of the comprising Formula (XII) to the compound comprising Formula (XIII) may be about 1:0:1.1.

The method of Step (e) utilizes an acyl coupling reagent and a proton acceptor. Suitable acyl coupling reagents and proton acceptors are detailed above in Section (II)(a). In one preferred embodiment, the acyl coupling reagent is 1-ethyl-3-(3-dimethylaminopropyl) carbodiimide) or a salt thereof and the proton acceptor is 4-methyl morpholine.

Generally, the equivalent ratio of the comprising Formula (XII) to the acyl coupling reagent may range from about 1.0:1.0 to about 1.0:1.5. In various embodiments, equivalent ratio of the comprising Formula (XII) to the acyl coupling reagent may range from about 1.0:1.0 to about 1.0:1.5, from about 1.0:1.0 to about 1.0:1.3, or from about 1.0:1.2. In one preferred embodiment, equivalent ratio of the comprising Formula (XII) to the acyl coupling reagent may be about 1:0:1.1.

Generally, the equivalent ratio of the comprising Formula (XII) to the proton acceptor may range from about 1.0:1.0 to about 1.0:2.5. In various embodiments, equivalent ratio of the comprising Formula (XII) to the proton acceptor may range from about 1.0:1.0 to about 1.0:2.5, from about 1.0:1.0 to about 1.0:2.25, or from about 1.0:2.2. In one preferred embodiment, equivalent ratio of the comprising Formula (XII) to the proton acceptor may be about 1:0:2.1.

Step (e) comprises a solvent. Suitable solvents are detailed above in Section (II)(a). In one preferred embodiment, the solvent useful in Step (e) is dimethylformamide.

In general, the volume to weight ratio of the solvent to the compound comprising Formula (XII) will range from about 0.5:1 to about 500:1. In various embodiments, the volume to weight ratio of the solvent to the compound comprising Formula (XII) may range from about 0.5:1 to about 500:1, from about 2:1 to about 250:1, from about 5:1 to about 200:1, or from about 10:1 to about 50:1. In an exemplary embodiment, the volume to weight ratio of the solvent to the compound comprising Formula (XII) may range from about 12:1 to about 20:1.

In general, the reaction of Step (e) will be conducted at a temperature that ranges from about −20° C. to about 25° C. depending on the solvent utilized. In various embodiments, the temperature of the reaction may range from about −20° C. to about 25° C., from about −10° C. to about 20° C., or from about −5° C. to about 5° C. In one embodiment, the reaction may be conducted at temperature about 0° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 2 hours. In some embodiments, the duration of the reaction may range from about 5 minutes to about 30 minutes, from about 30 minutes to about 1 hours, or from about 1 hour to about 2 hours. In a preferred embodiment, the reaction may be allowed to proceed for about 1 hour. In this context, a "completed reaction" generally means that the reaction mixture contains a significantly diminished amount of the compound of Formula (XII). Typically, the amount of the compound of Formula (XII) remaining in the reaction mixture at the end of the reaction may be less than about 10%, less than about 5%, or less than about 2%.

The compound comprising Formula (XIV) may have a yield of at least about 60%. In various embodiments, the compound comprising Formula (XIV) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (XIV) may have a yield of about 91%.

Step (f)

Step (f) of the eight step method involves contacting the compound comprising Formula (XIV) with a proton acceptor forming a reaction mixture. Upon work-up and isolation, the compound comprising Formula (XV) is obtained. This method step is termed a "deprotection" reaction.

The compound comprising Formula (XIV) is described in more detail above.

Suitable proton acceptors are detailed above in Section (II)(b). In one preferred embodiment, the proton acceptor is NaOH or LiOH.

Generally, the equivalent ratio of the comprising Formula (XIV) to the proton acceptor may range from about 1.0:1.0 to about 1.0:5.0. In various embodiments, equivalent ratio of the comprising Formula (XIV) to the proton acceptor may range from about 1.0:1.0 to about 1.0:5.0, from about 1.0:1.0 to about 1.0:3.0, or from about 1.0:1.5. In one preferred embodiment, equivalent ratio of the comprising Formula (XIV) to the proton acceptor may be about 1:0:2.0.

Step (d) further comprises a solvent. Suitable solvents are detailed above in Section (II)(a). In one preferred embodiment, the solvent is a combination of methanol and water.

In general, the volume to weight ratio of the solvent to the compound comprising Formula (XIV) will range from about 0.5:1 to about 500:1. In various embodiments, the volume to weight ratio of the solvent to the compound comprising Formula (XIV) may range from about 0.5:1 to about 500:1, from about 5:1 to about 200:1, from about 10:1 to about 100:1, or from about 15:1 to about 50:1. In preferred embodiment, the volume to weight ratio of the solvent to the compound comprising Formula (XIV) may be about 20:1.

In general, the reaction of Step (f) will be conducted at a temperature that ranges from about 0° C. to about 50° C. depending on the solvent utilized. In various embodiments, the temperature of the reaction may range from about 0° C. to about 50° C., from about 10° C. to about 40° C., or from about 20° C. to about 30° C. In one embodiment, the reaction may be conducted at temperature about 23° C. (room temperature). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 30 minutes to about 4 hours. In some embodiments, the duration of the reaction may range from about 30 minutes to about 1 hour, from about 1 hour to about 2 hours, or from about 2 hours to about 4 hours. In a preferred embodiment, the reaction may be allowed to proceed for about 2 hour. In this context, a "completed reaction" generally means that the reaction mixture contains a significantly diminished amount of the compound of Formula (XIV). Typically, the amount of the compound of Formula (XIV) remaining in the reaction mixture at the end of the reaction may be less than about 10%, less than about 5%, or less than about 2%.

After the completion of Step (f), the pH of the reaction mixture is adjusted to a pH of less than about 6.0. In various embodiments, the pH is adjusted to less than about pH 6.0, less than about pH 5.0, less than about pH 4.0, less than about pH 3.0, less than about pH 2.0, or less than about pH 1.0. In one preferred embodiment, the pH is adjusted to a range from about pH 2.0 to a pH of about 2.5.

This pH adjustment uses an aqueous acid. Non-limiting examples of suitable acids may be HCl, $H_2SO_4$, acetic acid, methanesulfonic acid, or similar organic or inorganic acids. In one preferred embodiment, the acid useful is HCl.

The compound comprising Formula (XV) may have a yield of at least about 60%. In various embodiments, the compound comprising Formula (XV) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (XV) may have a yield of about 92%.

Step (g)

Step (g) of the eight step method involves contacting the compound of Formula (XV) with the compound comprising Formula (XVIa) or Formula (XVIb) in the presence of an acyl coupling reagent to form a reaction mixture. Upon work-up and isolation, the compound comprising formula (XVII) is obtained.

The compound comprising Formula (XVII) is described in more detail above.

The compound comprising Formula (XVIa) and Formula (XVIb) are described in more detail below:

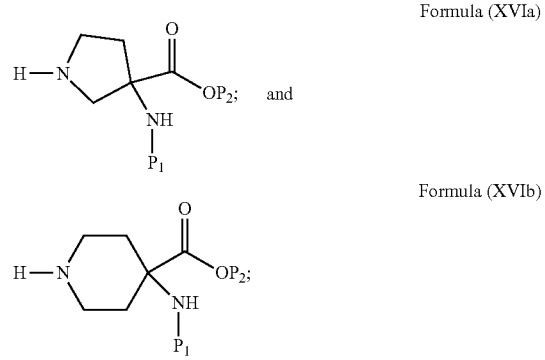

wherein $P_1$ is a nitrogen protecting group and $P_2$ is a carboxylic acid protecting group.

In specific embodiments, $P_1$ is a BOC group and $P_2$ is a methyl group. In one preferred embodiment, the compound comprising Formula (XVIa) is 3-(BOC-amino)pyrrolidine-3-carboxylic acid methyl ester and the compound comprising the Formula comprising (XVIb) is 4-(BOC-amino)piperidine-4-carboxylic acid methyl ester.

Generally, the equivalent ratio of the compound comprising Formula (XV) to either the compound comprising Formula (XVIa) or the compound comprising the formula (XVIb) may range from about 1.0:1.0 to about 1.0:1.5. In various embodiments, equivalent ratio of the compound comprising Formula (XV) to either the compound comprising Formula (XVIa) or the compound comprising the formula (XVIb) may range from about 1.0:1.0 to about 1.0:1.5, from about 1.0:1.0 to about 1.0:1.3, or from about 1.0:1.2. In one preferred embodiment, equivalent ratio of the compound comprising Formula (XVIa) or the compound comprising the formula (XVIb) may be about 1:0:1.2

The method of Step (g) utilizes an acyl coupling reagent and a proton acceptor. Suitable acyl coupling reagents and proton acceptors are detailed above in Section (II)(a). In one preferred embodiment, the acyl coupling reagent is 1-ethyl-3-(3-dimethylaminopropyl) carbodiimide) or a salt thereof and the proton acceptor is 4-methyl morpholine.

Generally, the equivalent ratio of the comprising Formula (XV) to the acyl coupling reagent may range from about 1.0:1.0 to about 1.0:1.5. In various embodiments, equivalent ratio of the comprising Formula (XV) to the acyl coupling reagent may range from about 1.0:1.0 to about 1.0:1.5, from about 1.0:1.0 to about 1.0:1.3, or from about 1.0:1.2. In one preferred embodiment, equivalent ratio of the comprising Formula (XV) to the acyl coupling reagent may be about 1:0:1.2.

Generally, the equivalent ratio of the comprising Formula (XV) to the proton acceptor may range from about 1.0:1.0 to about 1.0:2.5. In various embodiments, equivalent ratio of the comprising Formula (XV) to the proton acceptor may range from about 1.0:1.0 to about 1.0:2.5, from about 1.0:1.0 to about 1.0:2.25, or from about 1.0:2.2. In one preferred embodiment, equivalent ratio of the comprising Formula (XV) to the proton acceptor may be about 1:0:2.1.

Step (g) comprises a solvent. Suitable solvents are detailed above in Section (II)(a). In one preferred embodiment, the solvent useful in Step (g) is dimethylformamide.

In general, the volume to weight ratio of the solvent to the compound comprising Formula (XV) will range from about 0.5:1 to about 500:1. In various embodiments, the volume to weight ratio of the solvent to the compound comprising Formula (XV) may range from about 0.5:1 to about 500:1, from about 2:1 to about 250:1, from about 5:1 to about 200:1, or from about 10:1 to about 50:1. In an exemplary embodiment, the volume to weight ratio of the solvent to the compound comprising Formula (XV) may range from about 15:1 to about 25:1.

In general, the reaction of Step (g) will be conducted at a temperature that ranges from about −20° C. to about 25° C. depending on the solvent utilized. In various embodiments, the temperature of the reaction may range from about −20° C. to about 25° C., from about −10° C. to about 20° C., or from about −5° C. to about 5° C. In one embodiment, the reaction may be conducted at temperature about 0° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 2 hours. In some embodiments, the duration of the reaction may range from about 5 minutes to about 30 minutes, from about 30 minutes to about 1 hours, or from about 1 hour to about 2 hours. In a preferred embodiment, the reaction may be allowed to proceed for about 1 hour. In this context, a "completed reaction" generally means that the reaction mixture contains a significantly diminished amount of the compound of Formula (XV). Typically, the amount of the compound of Formula (XV) remaining in the reaction mixture at the end of the reaction may be less than about 10%, less than about 5%, or less than about 2%.

The compound comprising Formula (XVII) may have a yield of at least about 60%. In various embodiments, the compound comprising Formula (XVII) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (XVII) may have a yield ranging from about 88 to 93%.

Step (h)

Step (h) involves contacting the compound comprising Formula (XVII) with a deprotection reagent comprising an acid forming a reaction mixture. Upon work-up and isolation, the compound comprising Formula (I) is obtained.

Step (h), after using the deprotection reagent comprising an acid and isolation of the compound comprising Formula (I), the method may further contact the compound comprising Formula (I) with a proton acceptor to remove the carboxylic acid protecting group.

The compound comprising Formula (XVII) is described in more detail above.

Various acids may be used in this method step. In various embodiments, the deprotection reagent comprising an acid may be in pure form or in aqueous form. Non-limiting acid may be hydrochloric acid, hydrogen chloride, sulfuric acid, methanesulfonic acid, or trifluoroacetic acid. In one preferred embodiment, the deprotection reagent comprising an acid is trifluoroacetic acid.

Generally, the volume to weight ratio of the deprotection reagent comprising an acid is used in excess.

Step (h) comprises a solvent. Suitable solvents are detailed above in Section (II)(a). In one preferred embodiment, the solvent useful in Step (h) is dichloromethane.

In general, the volume to weight ratio of the solvent to the compound comprising Formula (XVII) will range from about 0.5:1 to about 500:1. In various embodiments, the volume to weight ratio of the solvent to the compound comprising Formula (XVII) may range from about 0.5:1 to about 500:1, from about 2:1 to about 250:1, from about 5:1 to about 200:1, or from about 10:1 to about 100:1. In an exemplary embodiment, the volume to weight ratio of the solvent to the compound comprising Formula (XVII) may range from about 40:1 to about 80:1.

In general, the reaction of Step (h) will be conducted at a temperature that ranges from about −20° C. to about 25° C. depending on the solvent utilized. In various embodiments, the temperature of the reaction may range from about −20° C. to about 25° C., from about −10° C. to about 20° C., or from about −5° C. to about 5° C. In one embodiment, the reaction may be conducted at temperature about 0° C. The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 5 minutes to about 2 hours. In some embodiments, the duration of the reaction may range from about 5 minutes to about 30 minutes, from about 30 minutes to about 1 hours, or from about 1 hour to about 2 hours. In a preferred embodiment, the reaction may be allowed to proceed for about 1 hour. In this context, a "completed reaction" generally means that the reaction mixture contains a significantly diminished amount of the compound of Formula (XVII). Typically, the amount of the compound of Formula (XVII) remaining in the reaction mixture at the end of the reaction may be less than about 10%, less than about 5%, or less than about 2%.

The compound comprising Formula (I) may have a yield of at least about 60%. In various embodiments, the compound comprising Formula (I) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (I) may have a yield ranging from about 88 to 93%.

The second deprotection step utilizes a proton acceptor. Suitable proton acceptors are detailed above in Section (II)(b). In one preferred embodiment, the proton acceptor is NaOH or LiOH.

Generally, the equivalent ratio of the comprising Formula (I) to the proton acceptor may range from about 1.0:1.0 to about 1.0:20.0. In various embodiments, equivalent ratio of the comprising Formula (I) to the proton acceptor may range from about 1.0:1.0 to about 1.0:20.0, from about 1.0:5 to about 1.0:15.0, or from about 1.0:8.0 to about 1.0:12.0. In one preferred embodiment, equivalent ratio of the comprising Formula (XIV) to the proton acceptor may be about 1:0:10.0.

The second deprotection step in Step (h) further comprises a solvent.

Suitable solvents are detailed above in Section (II)(a). In one preferred embodiment, the solvent is a combination of methanol and water.

In general, the volume to weight ratio of the solvent to the compound comprising Formula (I) will range from about 0.5:1 to about 500:1 in the second deprotection step. In various embodiments, the volume to weight ratio of the solvent to the compound comprising Formula (I) may range from about 0.5:1 to about 500:1, from about 5:1 to about 200:1, from about 10:1 to about 100:1, or from about 15:1 to about 50:1. In preferred embodiment, the volume to weight ratio of the solvent to the compound comprising Formula (I) may be about 20:1 in the second deprotection step.

In general, the second deprotection step in Step (h) will be conducted at a temperature that ranges from about 0° C. to about 50° C. depending on the solvent utilized. In various embodiments, the temperature of the reaction may range from about 0° C. to about 50° C., from about 10° C. to about 40° C., or from about 20° C. to about 30° C. In one embodiment, the reaction may be conducted at temperature about 23° C. (room temperature). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as HPLC, TLC, or proton nuclear magnetic resonance (e.g., $^1$H NMR). The duration of the reaction may range from about 30 minutes to about 4 hours. In some embodiments, the duration of the reaction may range from about 30 minutes to about 1 hour, from about 1 hour to about 2 hours, or from about 2 hours to about 4 hours. In a preferred embodiment, the reaction may be allowed to proceed for about 2 hour. In this context, a "completed reaction" generally means that the reaction mixture contains a significantly diminished amount of the compound of Formula (I). Typically, the amount of the compound of Formula (I) remaining in the reaction mixture at the end of the reaction may be less than about 10%, less than about 5%, or less than about 2%.

After the completion of Step (h) with the proton acceptor, the pH of the reaction mixture is adjusted to a pH of less than about 6.0. In various embodiments, the pH is adjusted to less than about pH 6.0, less than about pH 5.0, less than about pH 4.0, less than about pH 3.0, less than about pH 2.0, or less than about pH 1.0. In one preferred embodiment, the pH is adjusted to a range from about pH 2.0 to a pH of about 2.5.

This pH adjustment uses an aqueous acid. Non-limiting examples of suitable acids may be HCl, $H_2SO_4$, acetic acid, methanesulfonic acid, or similar organic or inorganic acids.

The compound comprising Formula (I) may have a yield of at least about 60%. In various embodiments, the compound comprising Formula (I) may have a yield of at least about 60%, at least about 65%, at least about 70%, at least about 75%, at least about 80%, at least about 85%, at least about 90%, at least about 95%, or at least about 99%. In one preferred embodiment, compound comprising Formula (I) may have a yield ranging from about 60-70%.

(III) Pharmaceutical Compositions Compound Comprising Formula (I) or a Pharmaceutically Acceptable Salt of the Compound Comprising Formula (I).

Another aspect of the present disclosure comprises pharmaceutical composition comprising the compound comprising Formula (I) or a pharmaceutically acceptable salt of the compound comprising Formula (I) and at least one pharmaceutically acceptable excipient.

(a) Compound Comprising Formula (I) or a Pharmaceutically Acceptable Salt of the Compound Comprising Formula (I)

The compound comprising Formula (I) or a pharmaceutically acceptable salt of the compound comprising Formula (I) are detailed above in Section (I).

Generally, the amount of compound comprising Formula (I) or a pharmaceutically acceptable salt of the compound comprising Formula (I) used in the pharmaceutical composition can and will varying depending upon the age of the subject, and the number of doses used per day. Generally, the amount of compound comprising Formula (I) or a pharmaceutically acceptable salt of the compound comprising Formula (I) may range from about 1.0 mg to about 100 mg. In various embodiments, the compound comprising Formula (I) or a pharmaceutically acceptable salt of the compound comprising Formula (I) used in the pharmaceutical composition may range from about 1.0 mg to about 100 mg, from about 5 mg to about 75 mg, or from about 10 mg to about 20 mg.

(b) At Least One Excipient

The composition of the disclosure may further comprise a pharmaceutically acceptable excipient. Non-limiting examples of suitable pharmaceutically acceptable excipients include a diluent, a binder, a filler, a buffering agent, a pH modifying agent, a disintegrant, a dispersant, a preservative, a lubricant, taste-masking agent, a flavoring agent, a coloring agent, or a combination thereof. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate, or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The composition may be formulated into various dosage forms and administered by a number of different means that will deliver a therapeutically effective amount of the active ingredient. Such compositions may be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration may include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising Formula (I) or a pharmaceutically acceptable salt of the compound comprising Formula (I) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a composition comprising Formula (I) or a pharmaceutically acceptable salt of the compound comprising Formula (I) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the composition comprising at least one anti-viral therapeutic may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a composition comprising the compound comprising Formula (I) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211, and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration, and composition of lipid, concentration of multivalent cations, rate of mixing, presence of and concentration of solvent.

In another embodiment, a composition of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A composition comprising at least one anti-viral therapeutic derivative may be encapsulated in a microemulsion by any method generally known in the art.

In yet another embodiment, the composition comprising Formula (I) or a pharmaceutically acceptable salt of the compound comprising Formula (I) may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(c) Dosage Forms

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

(IV). Methods of Treating Kappa-Opiate Receptor Agonist Medical Disorders.

In yet another aspect of the present disclosure comprises methods of treating kappa-opiate receptor agonist medical disorders. The method comprising administering the pharmaceutical composition comprising Formula (I) or a pharmaceutically acceptable salt of the compound comprising Formula (I) to a subject in need thereof. The kappa opioid receptor agonists-related disease or disorder is pain, cardiovascular disease, pruritus, nausea, inflammatory diseases, spinal anesthesia, anti-tussive, stroke, hypoxic pulmonary hypertension, multiple sclerosis, addiction, and post-traumatic cartilage degeneration.

(a) Composition and Dosage Forms.

Compositions and dosage forms are described in more detail above in Section (III).

Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

The amount of agent that is administered to the subject can and will vary depending upon the type of agent, the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

(b) Subjects

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

Definitions

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R_1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (0), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. Where the moiety is an oxygen atom (and hence, forming a protected hydroxy), exemplary protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. When the moiety is a nitrogen atom (and hence, forming a protecting amine) exemplary protecting groups include benzyl, p-methoxyphenyl (PMP), 3,4-dimethoxybenxyl (PMB)), n-silyl groups, esters (e.g., benzoate (Bz), carbonyl (e.g. p-methoxybenzyl carbonyl (Moz), tert-butyloxycarbonyl (BOC), 9-fluorenylmethyloxycarbonyl (FMOC)), acetyl, carbamates, n-silyl groups and the like. When the moiety is a carboxyl group, exemplary protecting groups include esters (methyl, substituted methyl ester, ethyl esters, substituted etyl esters) an alike. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro and thio.

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described methods without departing from the scope of the invention, it is intended that all matter contained in the above description and in the examples given below, shall be interpreted as illustrative and not in a limiting sense.

Example 1: Synthesis of Dipeptide Intermediate (3)

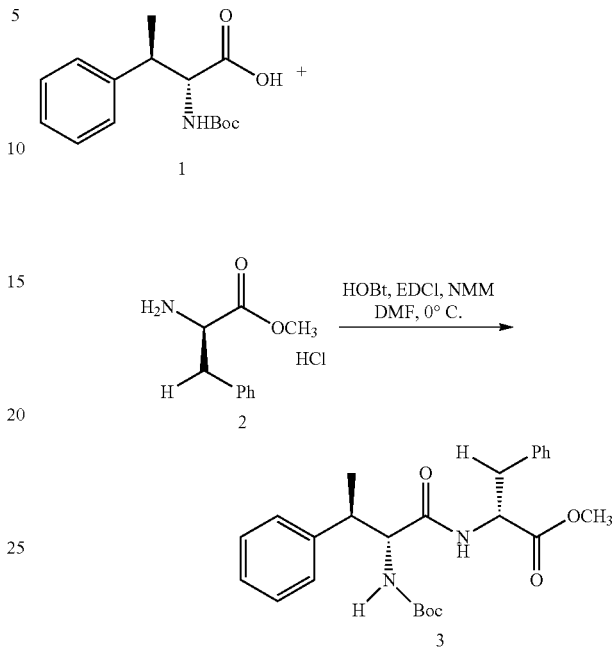

To the reaction flask were added (2R,3R)-Boc-beta-methyl-phenylalanine (1) (15 g, 36.1 mmol, 1.0 eq) and DMF (212 mL) under nitrogen. After the mixture became homogeneous under stirring, the resulting solution was cooled to 0° C. in ice bath. To the cooled reaction was added HOBt.H$_2$O (5.36 g, 39.7 mmol, 1.1. eq.) and N-ethyl-N'-(3-dimethylaminopropyl)carbodiimide hydrochloride (EDCl) (7.60 g, 39.7 mmol, 1.1 eq). The resulting mixture was stirred for 30 minutes, then H-D-Phe-OMe.HCl (2) (8.56 g, 39.7 mmol, 1.1 eq) and N-methylmorpholine (NMM) (7.58 mL, 75.7 mmol, 2.1 eq) were added. The reaction was stirred at 0° C. for one hour, and then stirred at room temperature until HPLC analysis indicated the reaction was complete. The reaction solution was added dropwise to water (600 mL) under stirring. After the water addition was complete, stirring was stopped and a precipitate began to form. The reaction mixture stood for 1 hour where the precipitation ceased. The precipitate (crystals) were collected by filtration and washed with water (400 mL×3), then dried in vacuum; the product (3) was obtained as a white solid, 14.36 g, yield=90.8%. LCMS: m/z=441.5 [M+H]$^+$.

Example 2: Synthesis of Dipeptide Intermediate (4)

-continued

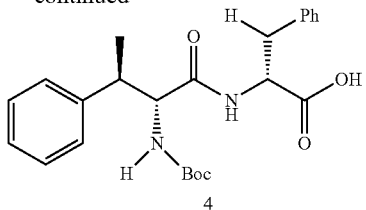

4

Into a reaction flask was added compound (3) (12 g, 27.2 mmol, 1.0 eq) and methanol (240 mL). Stirring was initiated and to the resulting solution was added NaOH solution (60 mL, 1 M, 60 mmol). The reaction mixture was stirred at room temperature for about 2 hours until HPLC analysis indicated the reaction was complete. To the reaction mixture was added HCl solution (1.0 M) dropwise until the pH of 2.0~2.5 was achieved. Then, water (380 mL) was added dropwise to precipitate the product. The resulting mixture stood for one hour, then the solid was collected by filtration and washed with water (3×320 mL), then dried under vacuum (30° C.). The product was obtained as white solid, 11 g, yield=94.8%. LCMS m/z=427.5 [M+H]$^+$.

Example 3: Synthesis of Tripeptide Intermediate (6)

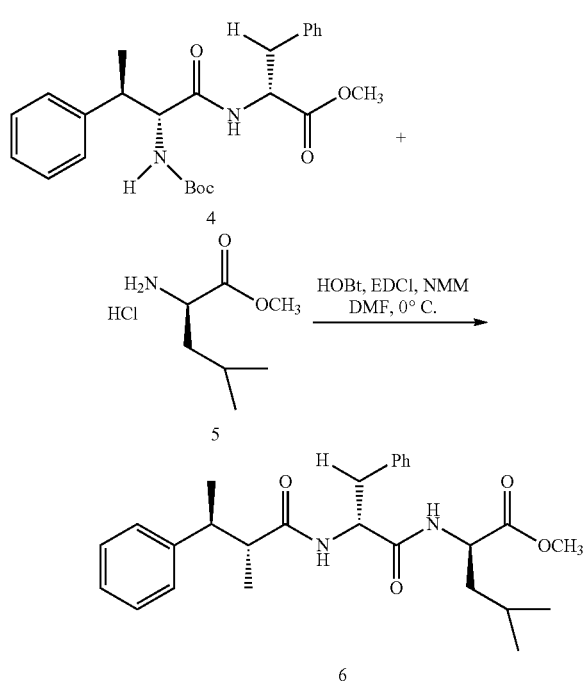

Into a reaction flask was added compound (4) (8.0 g, 18.8 mmol, 1.0 eq) and DMF (169 mL) under nitrogen. The resulting solution was cooled to 0° C. in ice bath. To the cooled reaction mixture was added HOBt. H$_2$O (2.79 g, 20.6 mmol, 1.2 eq) and EDCl (3.96 g, 20.5 mmol, 1.1 eq). After the reaction mixture was stirred at 0° C. for 30 minutes, H-D-Leu-OMe-HCl (5) (20.6 mmol, 1.1 eq, 3.75 g) and N-methylmorpholine (NMM) (3.94 mL, 39.4 mmol, 2.1 eq) were added. The resulting reaction mixture was stirred for 1 hour at 0° C. then warmed to room temperature until HPLC analysis indicated the reaction was completed. The reaction mixture was added dropwise into water (360 mL) with stirring. After the water addition was completed, stirring was stopped and a precipitate formed. The reaction mixture stood for one hour where the precipitation ceased. The precipitate was then collected by filtration and washed with water (240 mL×3), then dried in vacuum (30° C.); the product (6) was obtained as a white solid, 9.96 g, yield=96%. LCMS: m/z=554.7 [M+H]$^+$.

Example 4: Synthesis of Tripeptide Intermediate (7)

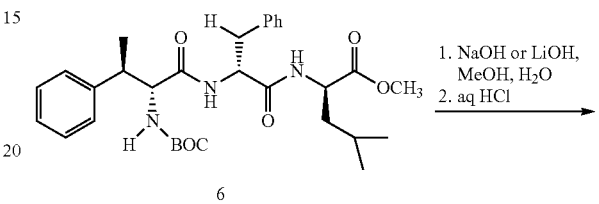

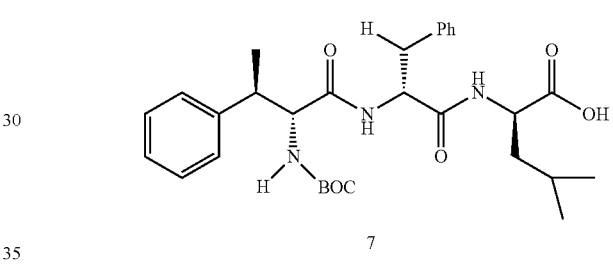

Into a reaction flask was added compound (6) (8 g, 14.4 mmol, 1.0 eq) and methanol (160 mL) under nitrogen. Stirring was initiated and then a NaOH solution (40 mL, 1 M, 40 mmol) was added. The reaction mixture was stirred at room temperature about 2 hours until HPLC analysis indicated the reaction was complete. Into the reaction mixture was added HCl solution (1.0 M) dropwise until the pH of 2.0~2.5 was achieved. Then, water (320 mL) was added dropwise to precipitate product. The reaction mixture stood for one hour, and then the solids were collected by filtration, washed with water (3×210 mL), and then dried under vacuum (30° C.). The product (7) was obtained as white solid, 7.41 g, yield=95%. LCMS m/z=540.7 [M+H]$^+$.

Example 5: Synthesis of Tetrapeptide Intermediate (9)

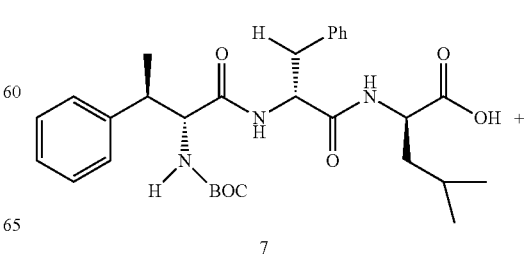

7

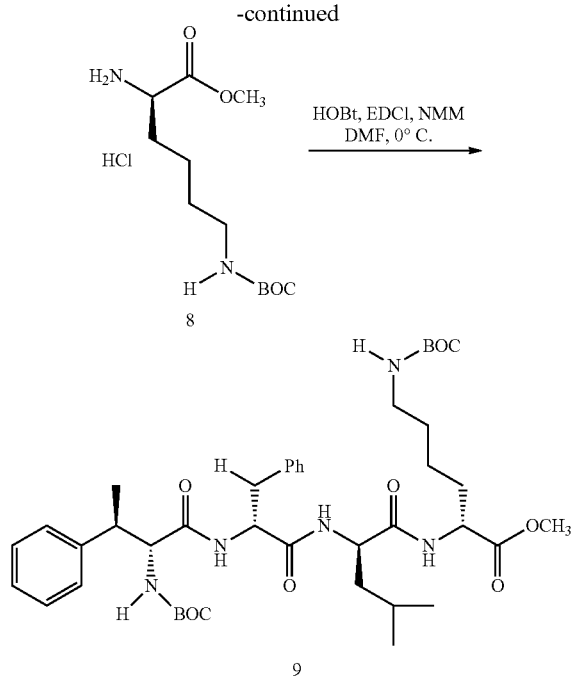

Into a reaction flask under nitrogen was added compound (7) (6.0 g, 11.1 mmol, 1.0 eq) and DMF (127 mL) under nitrogen. The resulting reaction mixture was cooled to 0° C. in ice bath. To the cooled reaction mixture was added HOBt.H₂O (1.81 g, 13.4 mmol, 1.2 eq) and EDCl (2.57 g, 13.4 mmol, 1.2 eq). After 30 minutes, H-D-Lys(Boc)-OMe-HCl (8) (3.97, 13.7 mmol, 1.2 eq) and N-methylmorpholine (NMM) (2.37 g, 23.4 mmol, 2.1 eq) were added. The reaction mixture was stirred at 0° C. for one hour and then warmed to room temperature until HPLC analysis indicated the reaction was completed. The reaction solution was added dropwise into water (360 mL) with stirring. After addition was completed, stirring was stopped and a precipitate formed. The reaction mixture stood for one hour. The precipitate was collected by filtration, washed with water (240 mL×3), and then dried under vacuum (30° C.). The isolated product (9) was obtained as a white solid, 7.9 g, yield=91%. LCMS: m/z=783.0 [M+H]⁺.

Example 6: Synthesis of Tetrapeptide Intermediate (10)

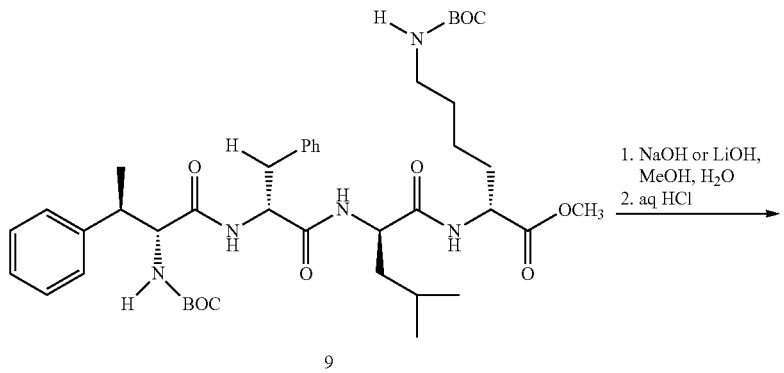

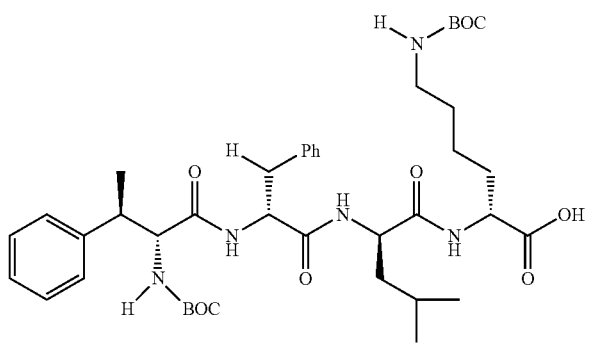

Into a reaction flask was added compound (9) (5 g, 6.39 mmol, 1.0 eq) and methanol (100 mL) under nitrogen. Stirring was initiated and a NaOH solution (25 mL, 1 M, 40 mmol) was added dropwise. The reaction mixture was stirred at room temperature about 2 hours until HPLC analysis indicated the reaction was completed. Then, an HCl solution (1.0 M) was added dropwise until a pH of 2.0~2.5 was achieved. The reaction mixture was added dropwise into water (200 mL) to precipitate the product. The resulting mixture stood for one hour. The solids were collected by filtration, washed with water (3×133 mL), and then dried under vacuum (30° C.). The product (10) was obtained as white solid, 4.51 g, yield=91.9%. LCMS m/z=769.0 [M+H]$^+$.

Example 7: Synthesis of Peptide Analog (12)

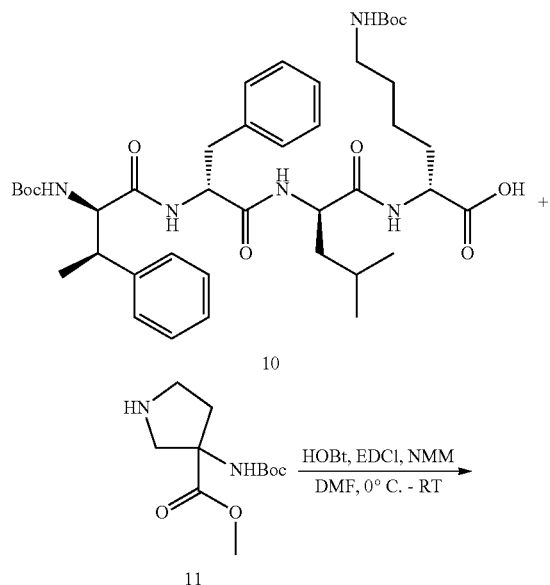

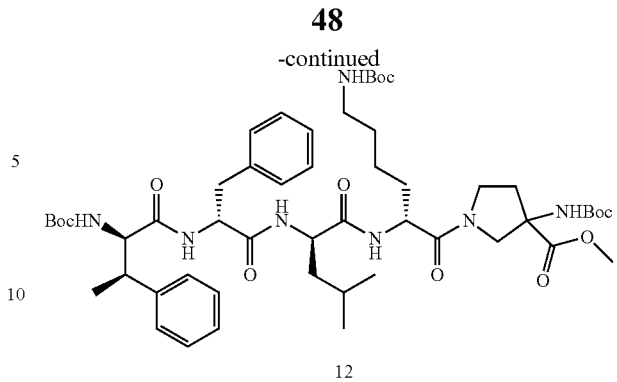

Into a reaction flask under nitrogen was added compound (10) (1.0 g, 1.3 mmol, 1.0 eq) and DMF (21 mL). The reaction mixture was cooled to 0° C. in ice bath. To the reaction mixture was added HOBt. H$_2$O (211 mg, 1.56 mmol, 1.2 eq) and EDCl (299 mg, 1.56 mmol, 1.2 eq). After stirring the reaction mixture at 0° C. for 30 minutes, 3-(Boc-amino)pyrrolidin-3-carboxylic methyl ester (11) (1.56 mmol, 1.2 eq, 381.1 mg) and N-methylmorpholine (NMM) (2.37 g, 23.4 mmol, 2.1 eq) were added. The reaction was stirred at 0° C. for one hour and warmed to room temperature until HPLC analysis indicated the reaction was complete. The reaction was added dropwise into water (60 mL) with stirring. After the addition was completed, stirring was stopped. The reaction mixture stood for one hour. The solids were then collected by filtration, washed with water (40 mL×3), and then dried under vacuum (30° C.). The product (12) was obtained as a white solid, 1.2 g, yield=93.1%. LCMS: m/z=995.2 [M+H]$^+$.

Example 8 Synthesis of Peptide Analogue (13)

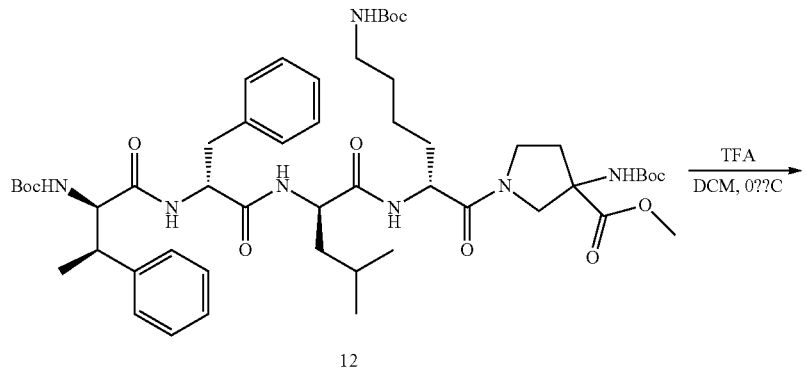

-continued

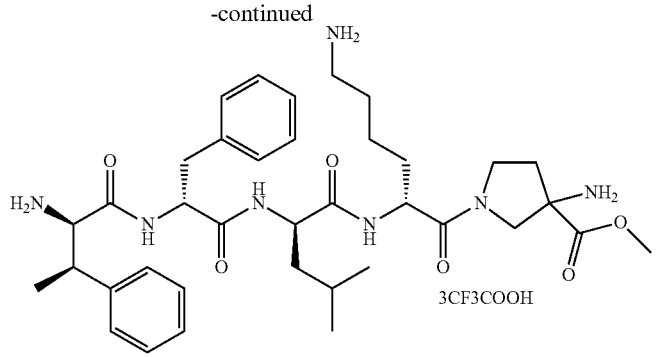

13

Into a reaction flask was added compound (12) (200 mg, 0.201 mmol, 1 eq) and dichloromethane (4 mL) under nitrogen. The resulting solution was cooled to −10° C. To the reaction mixture was added a mixture of trifluoroacetic acid (TFA, 4 mL) and dichloromethane (8 mL). The reaction was then stirred at −10° C. for one hour until HPLC analysis indicated the reaction was completed. The volatile organic materials were removed on a rotoevaporator. The residue was dissolved in dichloromethane (4 mL) and the resulting solution was distilled to dryness on a rotoevaporator. This process was repeated three additional times. The residue was dissolved in methanol (4 mL) and the resulting solution was evaporated to dryness on a rotoevaporator. This process was repeated three additional times. The obtained residue was purified on reverse phase HPLC, which provided the product (13) as a white solid, 135.4 mg, yield=65%. LCMS: MS m/z=694.4 [M+H]⁺.

Example 9 Synthesis of Peptide Analogue (14)

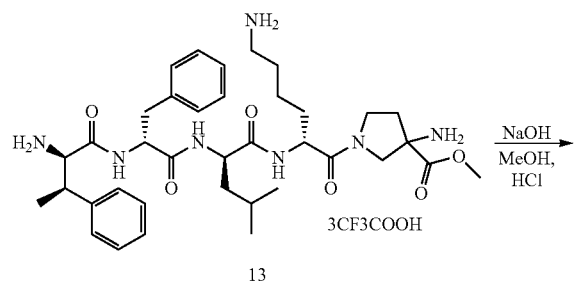

Into the reaction flask was added compound (13) (100 mg, 0.0965 mmol, 1 eq), and methanol (2 mL) under nitrogen. To the reaction mixture was added a solution of NaOH (0.5 mL, 1.0 M, 1.0 mmol), 10 eq.) dropwise. The reaction mixture was stirred at room temperature for 2 hours until HPLC analysis indicated the reaction was completed. Into the reaction mixture was added HCl solution (1.0 M) dropwise until a pH=2.0~2.5 was achieved. The volatile organic materials were removed on a rotoevaporator. The residue was purified on reverse phase HPLC with 0.1% TFA acetonitrile/water as mobile phase. The collected fractions were lyophilized to produce the product (14) as a white solid, 45.7 mg, yield=60%. LC-MS m/z=680.5 [M+H]⁺.

Example 9 Synthesis of Peptide Analogue (16)

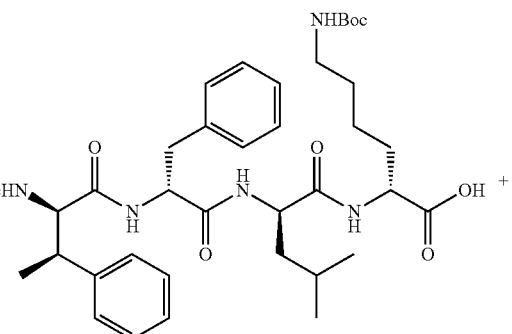

10
RFCX0139-30
$C_{41}H_{61}N_5O_9$
MW: 767.97

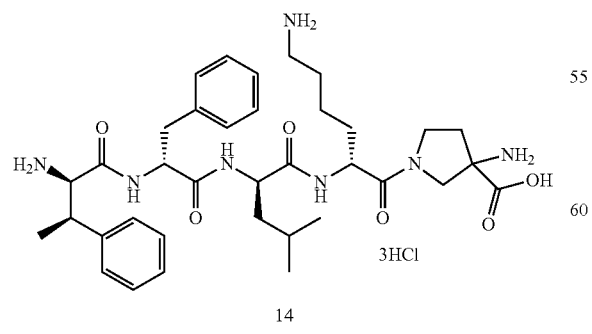

14

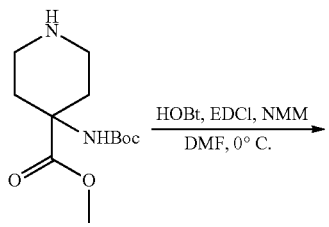

15
$C_{12}H_{22}N_2O_4$
MW 258.32

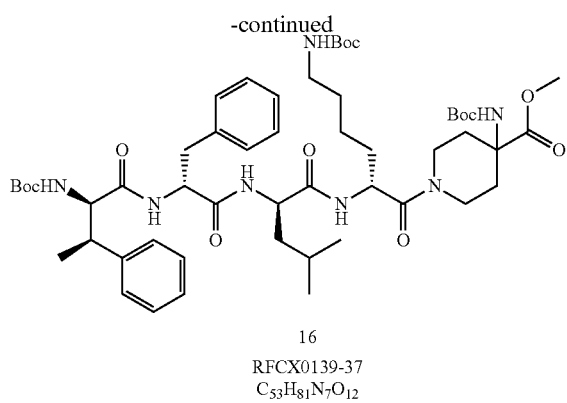

16
RFCX0139-37
$C_{53}H_{81}N_7O_{12}$
MW: 1008.27

Into a reaction flask under nitrogen was added compound (10) (1.0 g, 1.3 mmol, 1.0 eq) and DMF (21 mL). The reaction mixture was cooled to 0° C. in ice bath. Into the reaction mixture was added HOBt. H₂O (211 mg, 1.56 mmol, 1.2 eq) and EDCl (299 mg, 1.56 mmol, 1.2 eq). After stirring at 0° C. for 30 minutes, 4-(Boc-amino)piperidine-4-carboxylic acid methyl ester (15) (402.9 mg, 1.56 mmol, 1.2 eq) and N-methylmorpholine (NMM) (0.273 mL, 2.73 mmol, 2.1 eq) were added. The reaction mixture was stirred at 0° C. for one hour and warmed to room temperature until HPLC analysis indicated the reaction was completed. The reaction mixture was added dropwise into water (60 mL) with stirring. After addition was completed, stirring was stopped and a precipitate formed. The reaction mixture stood for one hour. The solid was then collected by filtration, washed with water (40 mL×3), and then dried under vacuum (30° C.). The product (16) was obtained as a white solid, 1.17 g, yield=87.5%. LCMS: m/z=1009.3 [M+H]⁺.

Example 10 Synthesis of Peptide Analogue (17)

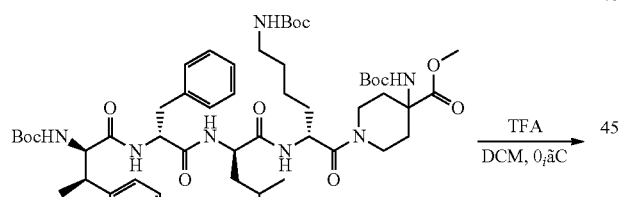

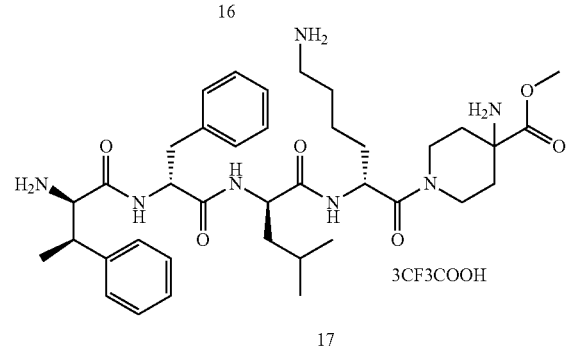

17

Into the reaction flaks was added compound (16) (500 mg, 0.496 mmol, 1 eq) and dichloromethane (10 mL) under nitrogen. The reaction mixture was cooled to −10° C. To the reaction mixture was added a mixture of TFA (10 mL) and dichloromethane (20 mL) dropwise. The reaction mixture was then stirred at −10° C. for one hour until HPLC analysis indicated the reaction was completed. The volatile organic materials were removed on a rotoevaporator. The residue was dissolved in dichloromethane (10 mL) and distilled to dryness on rotoevaporator. This process was repeated three additional times. The residue was dissolved in methanol (10 mL) and evaporated to dryness on a rotoevaporator. This process was repeated three time. The obtained residue was purified on reverse phase HPLC with 0.1% TFA acetonitrile/water as mobile phase. The collected fraction was lyophilized which provided the product (17) a white solid, 364.5 mg, yield=70%. LCMS: MS m/z=708.5 [M+H]⁺.

Example 11 Synthesis of Peptide Analogue (18)

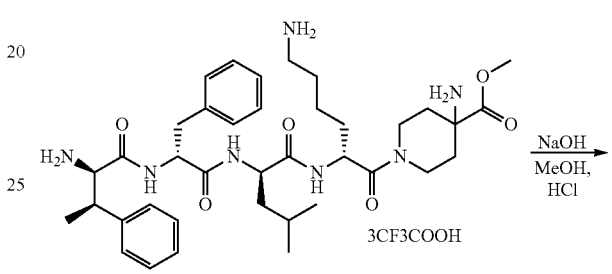

17
RFCX0139-43
$C_{44}H_{60}F_9N_7O_{12}$
MW: 1049.99

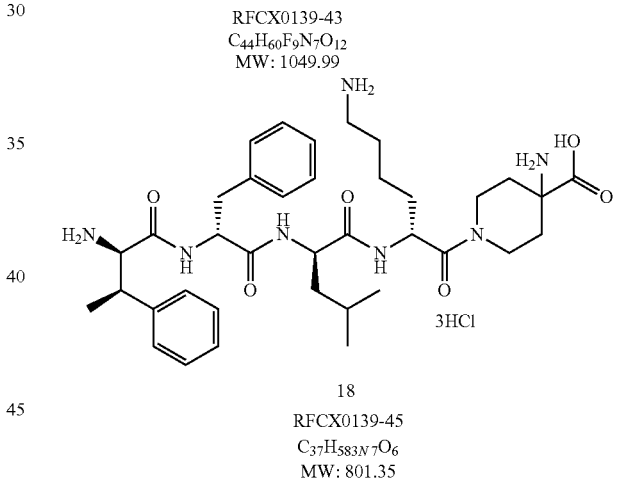

18
RFCX0139-45
$C_{37}H_{58}3_N7O_6$
MW: 801.35

Into a reaction flask was added compound (17) (100 mg, 0.0952 mmol, 1 eq) and methanol (2 mL) under nitrogen. To the reaction mixture was added a solution of NaOH (0.5 mL, 1.0 M, 1.0 mmol), 10 eq.) dropwise. The reaction mixture was stirred at room temperature for 2 hours until HPLC analysis indicated the reaction was completed. Then, a HCl solution (1.0 M) was added dropwise until apH=2.0~2.5 was achieved. Methanol was removed on a rotoevaporatorator to form a residue. The reside was purified on reverse phase HPLC with 0.1% TFA acetonitrile/water as mobile phase. The collected fractions were lyophilized to form the product (18) as a white solid, 45.8 mg, yield=60%. LC-MS m/z=802.3 [M+H]⁺.

Example 12: Opioid Receptor Binding Assay

The measurement of opioid receptor binding affinity was conducted using a radioligand binding assay on the membranes prepared from HEK293 cells (human embryonic kidney cell line) that were heterologously expressed for the recombinant human mu, delta or kappa opioid receptors.

The assay buffers used for opioid receptor binding studies were 50 mM Tris.HCl (pH 7.4) for KOR, 50 mM Tris.HCl (pH 7.4) with 5 mM $MgCl_2$ for MOR, and 50 mM Tris.HCl (pH 7.4) with 10 mM $MgCl_2$ plus 1 mM EDTA for DOR. The wash buffer solution contained 50 mM Tris.HCl with pH 7.4.

non-linear curve fitting routines in Prism®. Calculation of the inhibition was conducted using following equation:

$$\% \text{ Inhibition} = (1 - (\text{Assay well} - \text{Average\_LC})/(\text{Average\_HC} - \text{Average\_LC})) * 100\%$$

Binding data was analyzed using GraphPad Prism 5.0 and $IC_{50}$ data was generated by non-linear regression from dose response curves. Use the model "log (inhibitor) vs. response—Variable slope" was used to fit the data. This data is shown in Table 1.

TABLE 1

Binding Affinity of Peptide Ligands on Recombinant Human Opioid receptors

| # | Sample ID | KOR, $IC_{50}$(nM) | MOR, $IC_{50}$(nM) | DOR, $IC_{50}$(nM) | μ/k | δ/k |
|---|---|---|---|---|---|---|
| 1 | U-50488 | 3.197 | | | | |
| 2 | DAMGO | | 0.2938 | | | |
| 3 | Naltrindole | | | 0.158 | | |
| 4 | 13 | 0.2546 | 4109 | >10000 | 16139 | >39277 |
| 5 | 14 | 0.3981 | >10000 | >10000 | >25119 | >25118 |
| 6 | 17 | 0.1570 | 5381 | >10000 | 3427 | >63694 |
| 7 | 18 | 0.2525 | 9811 | >10000 | 38855 | >39603 |

The opioid receptor binding affinity were compared to three known standards: Naltrindole, U-50488 (trans-(+)-3,4-dichloro-N-methyl-N-[2-(1-pyrrolidinyl)cyclohexyl]phenylacetamide, see M. Doi, T. Ishida and M, Inoue; Structure of K-agonist, U-50488 Acta Cryst. (1990). C46, 676-678), and DAMGO (D-Ala2 MePhe4,Gly(ol)5]encephalin, see Allan D. Blake, George Bot, John C. Freeman, and Terry Reisine‡ Differential Opioid Agonist Regulation of the Mouse m Opioid Receptor* THE JOURNAL OF BIOLOGICAL CHEMISTRY Vol. 272, No. 2, Issue of January 10, pp. 782-790, 1997).

The radio ligands were prepared at the final concentration of 0.5 nM for [$^3$H]DAMGO, 0.5 nM for [$^3$H]diprenorphine, and 0.5 nM for [$^3$H] DADLE, which were used as the competing radioligands for mu, kappa and delta receptor respectively.

Cell membrane of HEK293 cells transfected with opioid receptors was prepared in the amount of 20 ug of MOR, 6.7 ug of KOR and 6.7 ug of DOR per each well respectively. These membranes containing the receptor of interest were incubated with increasing concentrations of test compound in the presence of a single concentration of radioligand. The fixed concentration of the radioligand was used and serial dilutions of the test compound were prepared.

Testing started at 10 uM of testing compound to 4-fold serial dilution for 8-points detection. 1 μl of compounds/high control/low control was transferred in to the 96 well plates according to the plate map, and then 100 μl of membrane stock solution was dispensed into the plate followed by 100 μl of radio ligand solution. The well plated were incubated for 1 hour at room temperature with 300 rpm gentle agitation. Then, soaked the Unifilter-96 GF/C filter plates with 50 μl of 0.3% Poly ethyleneimine per well for at least 0.5 hour at room temperature, and filtered the reaction mixture through the plates using FilterMate™harvester, then wash each plate for four times with cold wash buffer. The filter plates are then dried for 1 hour at 50° C. After drying, the filter was sealed in polyethylene and adds 50 μl of Perkin Elmer Microscint 20 cocktail and the radioactivity counted in a Perkin Elmer MicroBeta2 counter.

Specific binding is determined by subtraction of the Bound CPM values in the presence of 50-100x excess of cold ligand. Data is fitted using the saturation analysis Example 13 FLIPR Calcium Assay in Whole Cells The FLIPR Calcium Assay was used to measure the ability of an opioid ligand to induce a functional response upon receptor binding. The opioid mu receptors (MORs), delta receptors (DORs) and kappa receptors (KORs) are G-protein coupled receptors (GPCRs) which play an important role in cell signaling. The receptor was activated by a ligand then triggering G-protein activation inside the cell. An activated G-protein induces various cascades of intracellular messengers including calcium flux. The functional cell-based assays evaluated the changes of intracellular calcium level which were detected through use of fluorescent calcium-sensitive reporter dyes. The basic system of performing a calcium mobilization assay includes the FLIPR Calcium Assay Kit and the FLIPR Tetra® System, which were used to observe changes in intracellular calcium levels and determine the dose-response in HEK293 cells transfected with the recombinant human mu, delta or kappa opioid receptors.

The cells used in the assay were grown in the culture medium of 88% DMEM which contains 10% FBS, 300 ug/mL G418, 2 ug/mL Blasticidin, 1% GlutaMax and 1% Penicillin/Streptomycin (Hyclone-SV30010). Seeded 20000 cells in 20 uL medium to each well of assay plate (Greiner-781946), and the cells were maintained at 37° C. in an incubator with 5% $CO_2$ for 20 hours. The compound was then prepared at 5-fold serial dilution to get 10 doses and 500 nL of each concentration and was transferred into the compound plate. Then, 30 uL assay buffer (20 mM HEPES and 1×HBSS) was added to each well of compound plate and the plate was spun at 1500 rpm for 15 seconds. Then, 20 uL of 2× Fluo-4 Direct™ No-wash Loading Buffer ((Invitrogen-F10471) was gently dispensed to each well of assay plate and was spun at 1000 rpm for 15 seconds and then incubated at 37° C. for 50 min. The assay plate was removed from the incubator and placed at room temperature for 10 min. The assay plate, compound plate, and tip box were placed directly into the FLIPR Tetra® System. 10 uL of each compound was transferred from compound plate to the assay plate in FLIPR Tetra Fluorometric Imaging Plate Reader. The plate was for 140 times; then calculated the "Max-Min" starting from Read 1 to 140 to generate the final signal for % Effect calculation. The data was analyzed using Prism, curve fitting equation "log(agonist) vs. response—Variable slope". Table 2 shows the results of these assays.

TABLE 2

| Opioid Kappa Receptor Agonist FLIPR ASSAY | | | | | | |
|---|---|---|---|---|---|---|
| # | 1 | 2 | 3 | 4 | 5 | 6 |
| Sample ID | U69593 | nor-Binaltorphimine dihydrochloride | 13 | 14 | 17 | 18 |
| $EC_{50}$ (nM) | 96 | >720 | 7.588 | 9.859 | 9.377 | 5.218 |

What is claimed is:

1. A compound of Formula (I) or a pharmaceutically acceptable salt thereof:

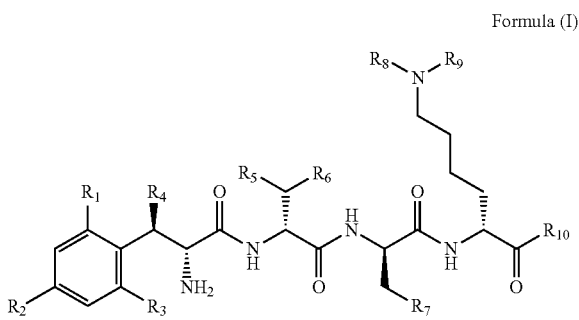

Formula (I)

wherein:

$R_1$, $R_2$, and $R_3$ are independently selected from a group consisting of H, CN, CI, F, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;

$R_4$ is selected from a group consisting of $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;

$R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, $C_3$-$C_{10}$ substituted cycloalkyl; unsubstituted aryl, substituted aryl, and substituted heterocyclic;

$R_7$ is selected from a group consisting of H, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;

$R_8$ and $R_9$ are independently selected from a group consisting of H, $C_1$-$C_8$ unsubstituted alkyl, $C_1$-$C_8$ substituted alkyl, and O-substituted $C_1$-$C_8$ alkyl, $R_{10}$ is

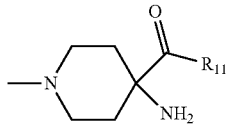

$R_{11}$ is selected from a group consisting of $OR_{12}$ and $NR_{13}R_{14}$;

$R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, $CH_3O(CH_2CH_2)_nCH_2CH_2$—, and $HO(CH_2CH_2)_nCH_2CH_2$—;

$R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, $CH_3O(CH_2CH_2)_nCH_2CH_2$—, and $HO(CH_2CH_2)_nCH_2CH_2$—; and n is an integer from 0 to 100;

wherein an unsubstituted alkyl, cycloalkyl, or aryl group comprises all carbon atoms, and a substituted alkyl, cycloalkyl, or aryl group comprises at least one nitrogen, oxygen, silicon, phosphorous, boron, or a halogen atom for at least one carbon atom.

2. The compound of claim 1, wherein $R_1$, $R_2$, and $R_3$ are independently selected from a group consisting of H, CN, $C_1$, F, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_4$ is selected from a group consisting of $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_5$ and $R_6$ are independently selected from a group consisting of H, $C_1$-$C_4$ unsubstituted alkyl, $C_1$-$C_4$ substituted alkyl, $C_3$-$C_8$ unsubstituted cycloalkyl, $C_3$-$C_8$ substituted cycloalkyl; unsubstituted aryl, substituted aryl, and substituted heterocyclic;

$R_7$ is selected from a group consisting of H, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_8$ and $R_9$ are independently selected from a group consisting of H, $C_1$-$C_4$ unsubstituted alkyl, $C_1$-$C_4$ substituted alkyl, and O-substituted $C_1$-$C_4$ alkyl;

$R_{10}$ is

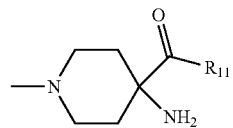

$R_{11}$ is selected from a group consisting of $OR_{12}$ and $NR_{13}R_{14}$;

$R_{12}$ is selected from a group consisting of H, $C_1$-$C_{12}$ unsubstituted alkyl, $C_1$-$C_{12}$ substituted alkyl, O-substituted $C_1$-$C_{12}$ alkyl, $CH_3O(CH_2CH_2)_n$ $CH_2CH_2$—, and $HO(CH_2CH_2)_n$ $CH_2CH_2$—;

$R_{13}$ and $R_{14}$ are independently selected from a group consisting of H, $C_1$-$C_{12}$ unsubstituted alkyl, $C_1$-$C_{12}$ substituted alkyl, O-substituted $C_1$-$C_{12}$ alkyl, $CH_3O(CH_2CH_2)_nCH_2CH_2$—, and $HO(CH_2CH_2)_nCH_2CH_2$—; and n is an integer from 0 to 50;

wherein an unsubstituted alkyl, cycloalkyl, or aryl group comprises all carbon atoms, and a substituted alkyl, cycloalkyl, or aryl group comprises at least one nitrogen, oxygen, silicon, phosphorous, boron, or a halogen atom for at least one carbon atom.

3. The compound of 2, wherein $R_1$, $R_2$, and $R_3$ are independently selected from a group consisting of H, Cl, F, methyl, ethyl, propyl, and iso-propyl;

$R_4$ is selected from a group consisting of, methyl, ethyl, propyl, iso-propyl, cyclopropyl, cyclobutyl, cyclopentyl, and cyclohexyl;

$R_5$ and $R_6$ are independently selected from a group consisting of H, methyl, ethyl, n-propyl, iso-propyl, cyclopropyl, cyclobutyl, cyclopentyl, cyclohexyl, and phenyl;

$R_7$ is selected from a group consisting of H, methyl, ethyl, propyl, iso-propyl, cyclopropyl, cyclobutyl, cyclopentyl, and cyclohexyl;

$R_8$ and $R_9$ are independently selected from a group consisting of H, methyl, ethyl, propyl, and iso-propyl;

$R_{10}$ is

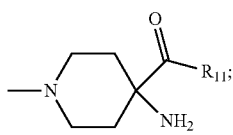

$R_{11}$ is selected from a group consisting of $OR_{12}$ and $NR_{13}R_{14}$, $R_{12}$ is selected from a group consisting of H, methyl, ethyl, n-propyl, and iso-propyl; and $R_{13}$ and $R_{14}$ are independently selected from a group consisting of H, methyl, ethyl, n-propyl, iso-propyl, cyclopropyl, cyclobutyl, cyclopentyl, and cyclohexyl.

4. The compound of claim 3, wherein $R_1$, $R_2$, $R_3$, $R_5$, $R_8$, and $R_9$ are H; $R_4$ is methyl; $R_6$ is phenyl; $R_7$ is iso-propyl; $R_{10}$ is

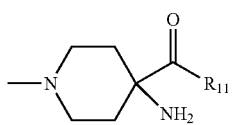

$R_{11}$ is $OR_{12}$; $R_{12}$ is H; and $R_{13}$, $R_{14}$, and n are absent as shown in the compound comprising Formula (IV):

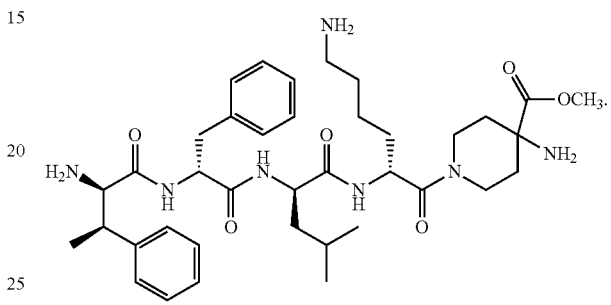

Formula (IV)

5. The compound of claim 3, wherein $R_1$, $R_2$, $R_3$, $R_5$, $R_8$, and $R_9$ are H; $R_4$ is methyl; $R_6$ is phenyl; $R_7$ is iso-propyl;

$R_{10}$ is

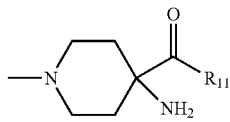

$R_{11}$ is $OR_{12}$; $R_{12}$ is Me; and $R_{13}$, $R_{14}$, and n are absent as shown in the compound comprising Formula (V):

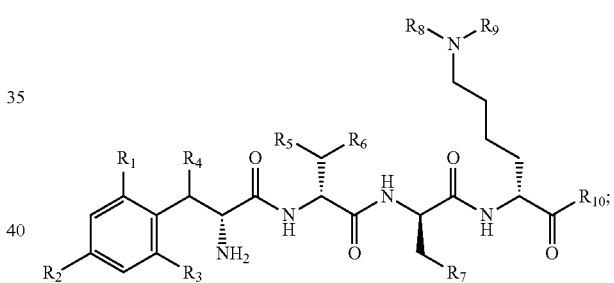

Formula (V)

6. A method of preparing the compound of Formula (I):

Formula (I)

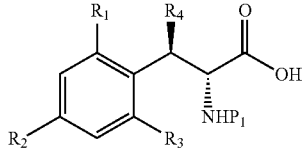

the method comprises:

a) contacting the compound comprising Formula (VI):

Formula (VI)

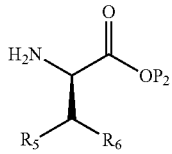

with the compound comprising Formula (VII):

Formula (VII)

in the presence of an acyl coupling reagent to form the compound comprising Formula (VIII):

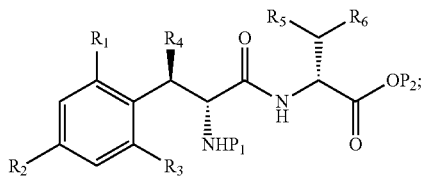
Formula (VIII)

b) contacting the compound comprising Formula (VIII) with a proton acceptor to form the compound comprising Formula (IX):

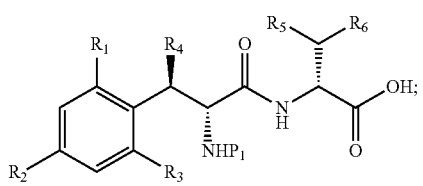
Formula (IX)

c) contacting the compound comprising Formula (IX) with the compound comprising Formula (X):

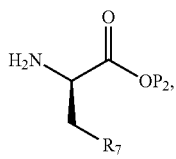
Formula (X)

in the presence of an acyl coupling reagent to form the compound comprising Formula (XI):

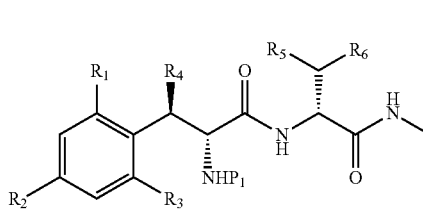
Formula (XI)

d) contacting the compound comprising Formula (XI) with a proton acceptor to form the compound comprising Formula (XII):

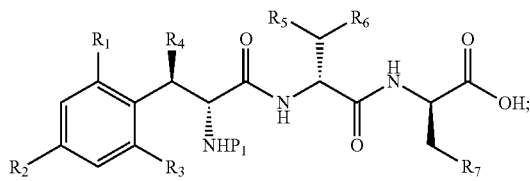
Formula (XII)

e) contacting the compound comprising Formula (XII) with the compound comprising Formula (XIII):

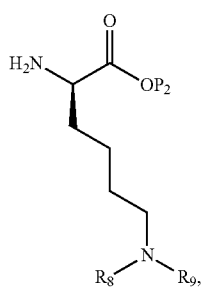
Formula (XIII)

in the presence on an acyl coupling reagent to form the compound comprising Formula (XIV):

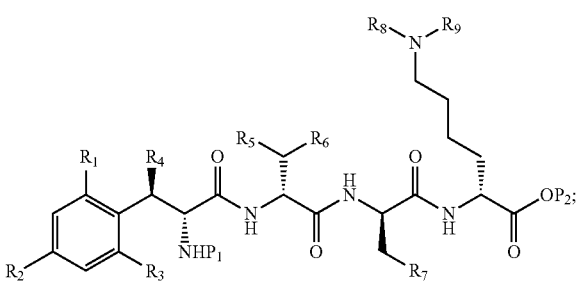
Formula (XIV)

f) contacting the compound comprising Formula (XIV) with a proton acceptor to form the compound comprising Formula (XV):

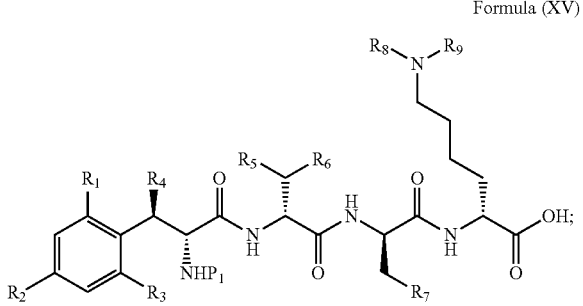
Formula (XV)

g) contacting the compound comprising Formula (XV) with the compound comprising Formula (XVIa) or Formula (XVIb):

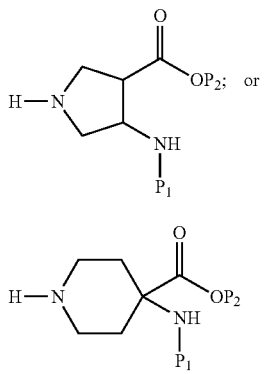

Formula (XVIa) or Formula (XVIb)

in the presence of an acyl coupling reagent to form the compound comprising Formula (XVII):

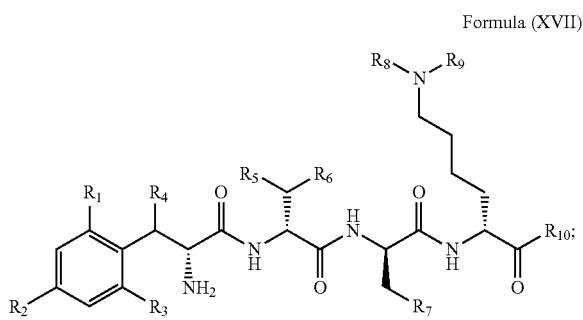

Formula (XVII)

and h) contacting the compound comprising Formula (XVII) with a deprotection reagent to form the compound comprising Formula (I);

wherein:

$R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;

$R_4$ and $R_7$ are independently selected from a group consisting of H, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;

$R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, $C_3$-$C_{10}$ substituted cycloalkyl; unsubstituted aryl, substituted aryl, and substituted heterocyclic;

$R_8$ and $R_9$ are independently selected from a group consisting of H, $C_1$-$C_8$ unsubstituted alkyl, $C_1$-$C_8$ substituted alkyl, O-substituted $C_1$-$C_8$ alkyl, $CH_3O(CH_2CH_2)_nCH_2CH_2$—, and $HO(CH_2CH_2)_nCH_2CH_2$—;

$R_{10}$ is selected from a group consisting of

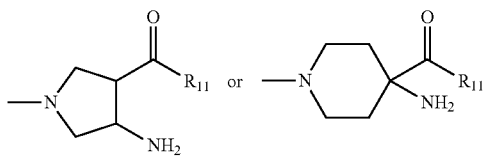

$R_{11}$ is selected from a group consisting of $OR_{12}$ and $NR_{13}R_{14}$, $R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, $(CH_3O(CH_2CH_2)_nCH_2CH_2$— and $HO(CH_2CH_2)_nCH_2CH_2$—;

$R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, $CH_3O(CH_2CH_2)_nCH_2CH_2$—, and $HO(CH_2CH_2)_nCH_2CH_2$—; and n is an integer from 0 to 100;

wherein an unsubstituted alkyl, cycloalkyl, or aryl group comprises all carbon atoms, and a substituted alkyl, cycloalkyl, or aryl group comprises at least one nitrogen, oxygen, silicon, phosphorous, boron, or a halogen atom for at least one carbon atom.

7. The method of claim 6, further comprising contacting the compound comprising Formula (I) with a proton acceptor.

8. The method of claim 6, wherein $P^1$ is a nitrogen protecting group and $P_2$ is a carboxylic acid protecting group.

9. The method of claim 8, wherein the nitrogen protecting group comprises a carbamate and the carboxylic acid comprises an ester.

10. The method of claim 8, wherein $P_1$ is a BOC group and $P_2$ is a methyl ester.

11. The method of claim 7, wherein $R_1$, $R_2$, and $R_3$ are independently selected from a group consisting of H, CN, Cl, F, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_4$ and $R_7$ are independently selected from a group consisting of H, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_5$ and $R_6$ are independently selected from a group consisting of H, $C_1$-$C_4$ unsubstituted alkyl, $C_1$-$C_4$ substituted alkyl, $C_3$-$C_8$ unsubstituted cycloalkyl, $C_3$-$C_8$ substituted cycloalkyl; unsubstituted aryl, substituted aryl, and substituted heterocyclic;

$R_8$ and $R_9$ are independently selected from a group consisting of H, $C_1$-$C_4$ unsubstituted alkyl, $C_1$-$C_4$ substituted alkyl, O-substituted $C_1$-$C_4$ alkyl, $CH_3O(CH_2CH_2)_nCH_2CH_2$—, and $HO(CH_2CH_2)_nCH_2CH_2$—;

$R_{10}$ is selected from a group consisting of

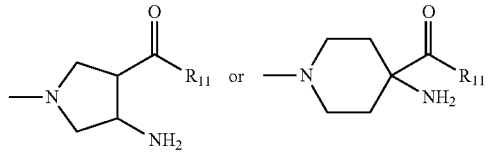

$R_{11}$ is selected from a group consisting of $OR_{12}$ and $NR_{13}R_{14}$, $R_{12}$ is selected from a group consisting of H, $C_1$-$C_{12}$ unsubstituted alkyl, $C_1$-$C_{12}$ substituted alkyl, O-substituted $C_1$-$C_{12}$ alkyl, $CH_3O(CH_2CH_2)_nCH_2CH_2$—, and $HO(CH_2CH_2)_nCH_2CH_2$—;

$R_{13}$ and $R_{14}$ are independently selected from a group consisting of H, $C_1$-$C_{12}$ unsubstituted alkyl, $C_1$-$C_{12}$ substituted alkyl, O-substituted $C_1$-$C_{12}$ alkyl, $CH_3O(CH_2CH_2)_nCH_2CH_2$—, and $HO(CH_2CH_2)_nCH_2CH_2$—; and n is an integer from 0 to 50;

wherein an unsubstituted alkyl, cycloalkyl, or aryl group comprises all carbon atoms, and a substituted alkyl, cycloalkyl, or aryl group comprises at least one nitrogen, oxygen, silicon, phosphorous, boron, or a halogen atom for at least one carbon atom.

12. The method of claim 11, wherein $R_1$, $R_2$, and $R_3$ are independently selected from a group consisting of H, Cl, F, methyl, ethyl, propyl, and iso-propyl;

$R_4$ and $R_7$ are independently selected from a group consisting of H, methyl, ethyl, propyl, and iso-propyl;

$R_5$ and $R_6$ are independently selected from a group consisting of H, methyl, ethyl, n-propyl, iso-propyl, cyclopropyl, cyclobutyl, cyclopentyl, cyclohexyl, and phenyl;

$R_8$ and $R_9$ are independently selected from a group consisting of H, methyl, ethyl, propyl, and iso-propyl;

$R_{10}$ is selected from a group consisting of

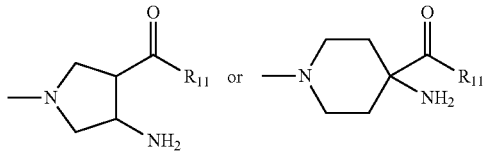

$R_{11}$ is selected from a group consisting of $OR_{12}$ and $NR_{13}R_{14}$;

$R_{12}$ is selected from a group consisting of H, methyl, ethyl, n-propyl, and iso-propyl;

$R_{13}$ and $R_{14}$ are independently selected from a group consisting of H, methyl, ethyl, n-propyl, iso-propyl, cyclopropyl, cyclobutyl, cyclopentyl, and cyclohexyl; and n is absent.

13. The method of claim 12, wherein $R_1$, $R_2$, $R_3$, $R_5$, $R_8$, and $R_9$ are H; $R_4$ is methyl; $R_6$ is phenyl; $R_7$ is iso-propyl;

$R_{10}$ is

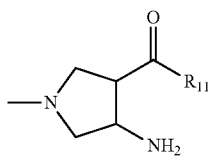

$R_{11}$ is $OR_{12}$; $R_{12}$ is H; and $R_{13}$, $R_{14}$, and n are absent as shown in the compound comprising Formula (II):

Formula (II)

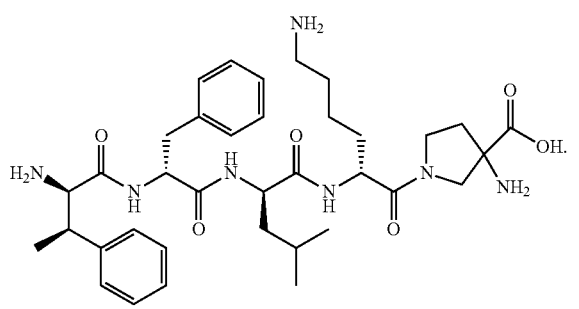

14. The method of claim 12, wherein $R_1$, $R_2$, $R_3$, $R_5$, $R_8$, and $R_9$ are H; $R_4$ is methyl; $R_6$ is phenyl; $R_7$ is iso-propyl;

$R_{10}$ is

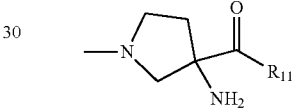

$R_{11}$ is $OR_{12}$; $R_{12}$ is Me; and $R_{13}$, $R_{14}$, and n are absent as shown in the compound comprising Formula (III):

Formula (III)

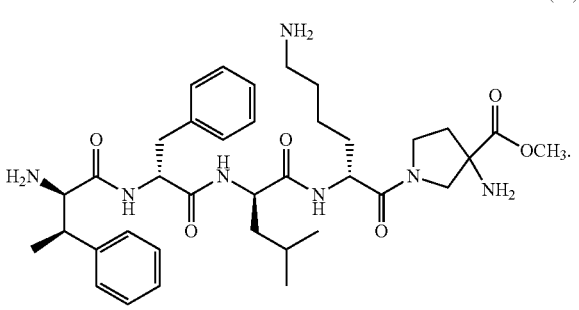

15. The method of claim 12, wherein $R_1$, $R_2$, $R_3$, $R_5$, $R_8$, and $R_9$ are H; $R_4$ is methyl; $R_6$ is phenyl; $R_7$ is iso-propyl;

$R_{10}$ is

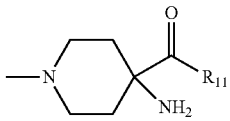

$R_{11}$ is $OR_{12}$; $R_{12}$ is H; and $R_{13}$, $R_{14}$, and n are absent as shown in the compound comprising Formula (IV):

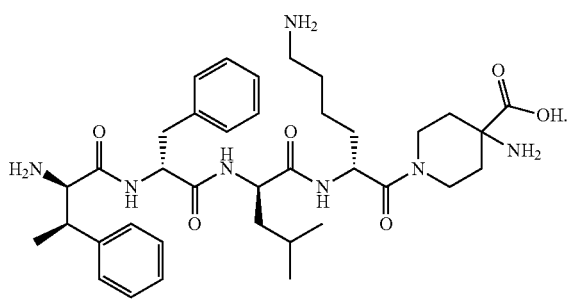

Formula (IV)

16. The method of claim 12, wherein
$R_1$, $R_2$, $R_3$, $R_5$, $R_8$, and $R_9$ are H; $R_4$ is methyl; $R_6$ is phenyl; $R_7$ is iso-propyl;
$R_{10}$ is

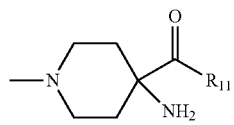

$R_{11}$ is $OR_{12}$; $R_{12}$ is Me; and $R_{13}$, $R_{14}$, and n are absent as shown in the compound comprising Formula (V):

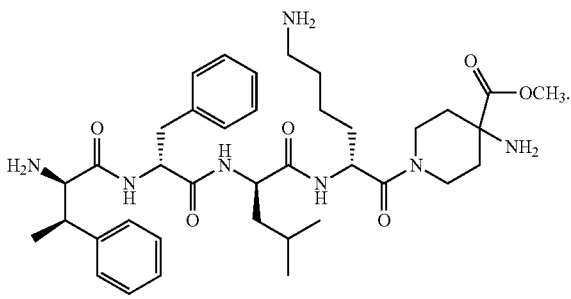

Formula (V)

17. A pharmaceutical composition comprising the compound comprising Formula (I) and at least one pharmaceutically acceptable excipient.

18. A compound of Formula (I) or a pharmaceutically acceptable salt thereof:

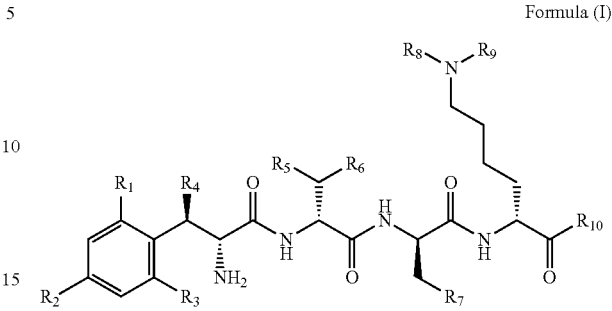

Formula (I)

wherein:
- $R_1$, $R_2$, and $R_3$ are independently selected from a group consisting of H, CN, Cl, F, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;
- $R_4$ is selected from a group consisting of H, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;
- $R_5$ and $R_6$ are independently selected from a group consisting of H, $C_1$-$C_8$ unsubstituted alkyl, $C_1$-$C_8$ substituted alkyl, $C_3$-$C_{10}$ unsubstituted cycloalkyl, $C_3$-$C_{10}$ substituted cycloalkyl; unsubstituted aryl, substituted aryl, and substituted heterocyclic;
- $R_7$ is selected from a group consisting of H, $C_1$-$C_8$ unsubstituted alkyl, $C_1$-$C_8$ substituted alkyl, $C_3$-$C_{10}$ unsubstituted cycloalkyl, and $C_3$-$C_{10}$ substituted cycloalkyl;
- $R_8$ and $R_9$ are independently selected from a group consisting of H, $C_1$-$C_8$ unsubstituted alkyl, $C_1$-$C_8$ substituted alkyl, O-substituted $C_1$-$C_8$ alkyl, $CH_3O(CH_2CH_2O)_nCH_2CH_2-$, and $HO(CH_2CH_2O)_nCH_2CH_2-$;
- $R_{10}$ is

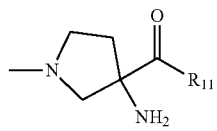

- $R_{11}$ is selected from a group consisting of $OR_{12}$ and $NR_{13}R_{14}$,
- $R_{12}$ is selected from a group consisting of H, $C_1$-$C_{24}$ unsubstituted alkyl, $C_1$-$C_{24}$ substituted alkyl, O-substituted $C_1$-$C_{24}$ alkyl, $CH_3O(CH_2CH_2O)_nCH_2CH_2-$, and $HO(CH_2CH_2O)_nCH_2CH_2-$;
- $R_{13}$ and $R_{14}$ are independently selected from a group consisting of H, $C_1$-$C_{24}$ unsubstituted alkyl, $C_1$-$C_{24}$ substituted alkyl, O-substituted $C_1$-$C_{24}$ alkyl, $CH_3O(CH_2CH_2O)_nCH_2CH_2-$, and $HO(CH_2CH_2O)_nCH_2CH_2-$; and
- n is an integer from 0 to 100;
wherein an unsubstituted alkyl, cycloalkyl, or aryl group comprises all carbon atoms, and a substituted alkyl, cycloalkyl, or aryl group comprises at least one nitrogen, oxygen, silicon, phosphorous, boron, or a halogen atom for at least one carbon atom.

19. The compound of claim 18, wherein $R_1$, $R_2$, and $R_3$ are independently selected from a group consisting of H, CN, CI, F, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_4$ is selected from a group consisting of H, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_5$ and $R_6$ are independently selected from a group consisting of H, $C_1$-$C_4$ unsubstituted alkyl, $C_1$-$C_4$ substituted alkyl, $C_3$-$C_8$ unsubstituted cycloalkyl, $C_3$-$C_8$ substituted cycloalkyl; unsubstituted aryl, substituted aryl, and substituted heterocyclic;

$R_7$ is selected from a group consisting of H, $C_1$-$C_4$ unsubstituted alkyl, $C_1$-$C_4$ substituted alkyl, $C_3$-$C_8$ unsubstituted cycloalkyl, and $C_3$-$C_8$ substituted cycloalkyl;

$R_8$ and $R_9$ are independently selected from a group consisting of H, $C_1$-$C_4$ unsubstituted alkyl, $C_1$-$C_4$ substituted alkyl, O-substituted $C_1$-$C_4$ alkyl, $CH_3O(CH_2CH_2O)_nCH_2CH_2-$, and $HO(CH_2CH_2O)_nCH_2CH_2-$ $R_{10}$ is

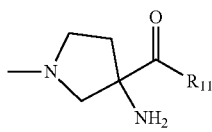

$R_{11}$ is selected from a group consisting of $OR_{12}$ and $NR_{13}R_{14}$, $R_{12}$ is selected from a group consisting of H, $C_1$-$C_{12}$ unsubstituted alkyl, $C_1$-$C_{12}$ substituted alkyl, O-substituted $C_1$-$C_{12}$ alkyl, $CH_3O(CH_2CH_2O)_nCH_2CH_2-$, and $HO(CH_2CH_2)_nCH_2CH_2-$ $R_{13}$ and $R_{14}$ are independently selected from a group consisting of H, $C_1$-$C_{12}$ unsubstituted alkyl, $C_1$-$C_{12}$ substituted alkyl, O-substituted $C_1$-$C_{12}$ alkyl, $CH_3O(CH_2CH_2O)_nCH_2CH_2-$, and $HO(CH_2CH_2O)_nCH_2CH_2-$; and n is an integer from 0 to 50;

wherein an unsubstituted alkyl, cycloalkyl, or aryl group comprises all carbon atoms, and a substituted alkyl, cycloalkyl, or aryl group comprises at least one nitrogen, oxygen, silicon, phosphorous, boron, or a halogen atom for at least one carbon atom.

20. The compound of claim 19, wherein $R_1$, $R_2$, and $R_3$ are independently selected from a group consisting of H, CI, F, methyl, ethyl, propyl, and iso-propyl;

$R_4$ and $R_7$ are independently selected from a group consisting of H, methyl, ethyl, propyl, iso-propyl, cyclopropyl, cyclobutyl, cyclopentyl, and cyclohexyl;

$R_5$ and $R_6$ are independently selected from a group consisting of H, methyl, ethyl, n-propyl, iso-propyl, cyclopropyl, cyclobutyl, cyclopentyl, cyclohexyl, and phenyl;

$R_8$ and $R_9$ are independently selected from a group consisting of H, methyl, ethyl, propyl, and iso-propyl;

$R_{10}$ is

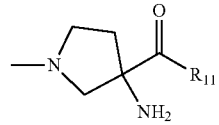

$R_{11}$ is selected from a group consisting of $OR_{12}$ and $NR_{13}R_{14}$, $R_{12}$ is selected from a group consisting of H, methyl, ethyl, n-propyl, and iso-propyl; and $R_{13}$ and $R_{14}$ are independently selected from a group consisting of H, methyl, ethyl, n-propyl, iso-propyl, cyclopropyl, cyclobutyl, cyclopentyl, and cyclohexyl.

21. The compound of claim 20, wherein $R_1$, $R_2$, $R_3$, $R_5$, $R_8$, and $R_9$ are H; $R_4$ is methyl; $R_6$ is phenyl; $R_7$ is iso-propyl;

$R_{10}$ is

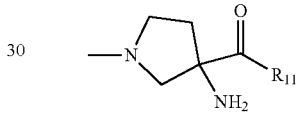

$R_{11}$ is $OR_{12}$; $R_{12}$ is H; and $R_{13}$, $R_{14}$, and n are absent as shown in the compound comprising Formula (II):

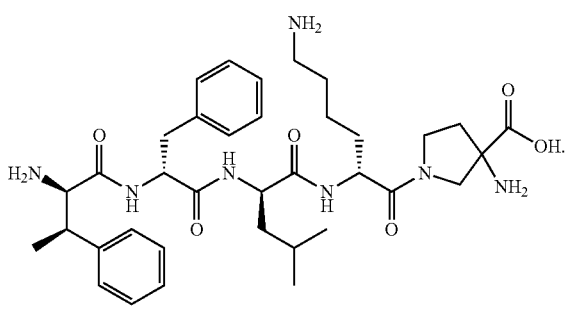

Formula (II)

22. The compound of claim 20, wherein $R_1$, $R_2$, $R_3$, $R_5$, $R_8$, and $R_9$ are H; $R_4$ is methyl; $R_6$ is phenyl; $R_7$ is iso-propyl;

$R_{10}$ is

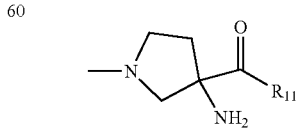

$R_{11}$ is $OR_{12}$; $R_{12}$ is Me; and $R_{13}$, $R_{14}$, and n are absent as shown in the compound comprising Formula (III):
Formula (III)
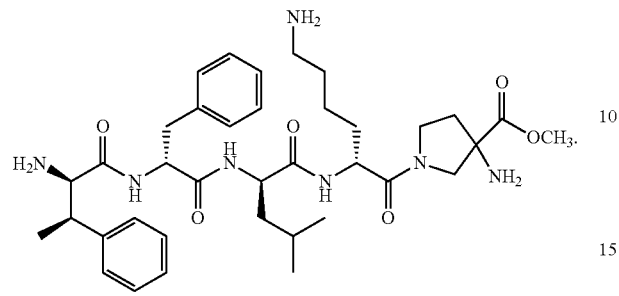
* * * * *